(12) United States Patent
Najib-Fruchart et al.

(10) Patent No.: US 7,375,135 B2
(45) Date of Patent: May 20, 2008

(54) FATTY ACID DERIVATIVES; PREPARATION AND USES THEREOF

(75) Inventors: Jamila Najib-Fruchart, Santes (FR); Karine Caumont-Bertrand, Frelinghien (FR)

(73) Assignee: Genfit, Loos (FR)

( * ) Notice: Subject to any disclaimer, the term of this patent is extended or adjusted under 35 U.S.C. 154(b) by 464 days.

(21) Appl. No.: 10/484,350

(22) PCT Filed: Aug. 8, 2002

(86) PCT No.: PCT/FR02/02831

§ 371 (c)(1), (2), (4) Date: Jan. 21, 2004

(87) PCT Pub. No.: WO03/014073

PCT Pub. Date: Feb. 20, 2003

(65) Prior Publication Data

US 2004/0192908 A1     Sep. 30, 2004

(30) Foreign Application Priority Data

Aug. 9, 2001 (FR) ................................. 01 10645

(51) Int. Cl.
*A61K 31/225* (2006.01)
*C07C 205/00* (2006.01)

(52) U.S. Cl. ...................... 514/547; 514/724; 560/125; 560/126; 560/128

(58) Field of Classification Search ................ 514/547, 514/724; 560/125, 126, 128
See application file for complete search history.

(56) References Cited

U.S. PATENT DOCUMENTS

| | | | |
|---|---|---|---|
| 2,010,154 | A | 8/1935 | Hubacher |
| 4,134,770 | A | 1/1979 | Emoto et al. |
| 5,093,365 | A | 3/1992 | Berg |
| 5,885,595 | A * | 3/1999 | Corey et al. .................. 424/401 |
| 6,117,904 | A * | 9/2000 | Murphy et al. .............. 514/547 |
| 2006/0035977 | A1 | 2/2006 | Najib |
| 2006/0069156 | A1 | 3/2006 | Darteil |
| 2006/0105987 | A1 | 5/2006 | Miller |
| 2006/0154984 | A1 | 7/2006 | Darteil |
| 2006/0252827 | A1 | 11/2006 | Darteil |

FOREIGN PATENT DOCUMENTS

| | | |
|---|---|---|
| DE | 20 28 240 A | 12/1970 |
| EP | 0 018 342 A | 10/1980 |
| EP | 0 447 553 A | 9/1991 |
| JP | 2000-169443 | 6/2000 |
| WO | 99/10321 | 3/1990 |
| WO | 97/03663 | 2/1997 |
| WO | 03/014073 | 2/2003 |

OTHER PUBLICATIONS

Gouw et al., 1967, CAS:67:12802.*
Grundland, 1950, CAS: 44:29936.*
Isa et al., 1989, CAS: 111:201395.*
Joly et al., 1938, CAS:32 :13997.*
Rabinowitz et al., 1963, CAS :59 :16669.*
Jart, 1962, CAS : 56 :36082.*
Uehara et al., 1986, CAS :105 :196991.*
Imai et al., 1998, CAS : 129 :113540.*
Or Livesey et al., 1988, CAS : 109 :109267.*
Database CAPLUS 'Online; Chemical Abstracts Service, Columbus, Ohio, US; Retrieved from STN, Database Accession No. 1983:18071, XP002203065.
L.P. Molleyres et al; J. Biol. Chem., vol. 263, No. 29, 1988, pp. 14832-14838, XP001042275.
K. Larsson; Acta Crystallogr.; vol. 16, 1963, pp. 741-748, XP000926795.
R. Li et al; J. Org. Chem., vol. 58, No. 7, 1993, pp. 1952-1954, XP002203063.
Chemical Abstracts, vol. 51, No. 13, Jul. 10, 1957, Columbus, Ohio, US; Abstract No. 9489f, XP002203064.
Database CAPLUS Online; Chemical Abstracts Service, Columbus, Ohio, US; Retrieved from STN, Database Accession No. 1976:151548, XP002203066.
T. Naalsund et al; Chemistry and Physics of Lipids, vol. 112, No. 1, 2001, pp. 59-65, XP000926796.
U. Heimann et al; Liebigs Ann. Chem., vol. 6, 1980, pp. 858-862, XP001042276.
File History of U.S. Appl. No. 10/504,482 obtained from U.S. PTO IFW on Jun. 22, 2007.
File History of U.S. Appl. No. 10/541,225 obtained from U.S. PTO IFW on Jun. 22, 2007.
File History of U.S. Appl. No. 10/542,056 obtained from U.S. PTO IFW on Jun. 22, 2007.
File History of U.S. Appl. No. 10/542,512 obtained from U.S. PTO IFW on Jun. 22, 2007.
International Search Report (French) for PCT/FR2004/000320 dated Oct. 5, 2004.
International Search Report of PCT/FR2004/000229, mailed Jul. 27, 2004.
Houte et al., Synthesis of structured lipids and etherlipids with antioxidants: combination of a selena fatty acid and a selena fatty alcohol with a carotenoic acid in glyceride molecules, *Chemistry and Physics of Lipids*, vol. 105, No. 1, 2000, pp. 105-113, XP002255207.

(Continued)

*Primary Examiner*—Rei-tsang Shiao
(74) *Attorney, Agent, or Firm*—Nixon & Vanderhye P.C.

(57) ABSTRACT

The invention concerns novel molecules, their preparation and their uses, in particular in the field of human and veterinary medicine and cosmetics. The inventive compounds are partly fatty acid derivatives and exhibit advantageous pharmacological and cosmetic properties. The invention also concerns various uses of said compounds, the pharmaceutical compositions containing them and methods for preparing them. The inventive compounds are useful in particular for preventing and/or treating dyslipidemiae, cardiovascular diseases, syndrome X, restenosis, diabetes, obesity, hypertension, certain cancers, dermatological diseases and in cosmetics, for fighting against skin aging and its effects notably against wrinkles and the like.

43 Claims, 13 Drawing Sheets

OTHER PUBLICATIONS

Figure 1A:
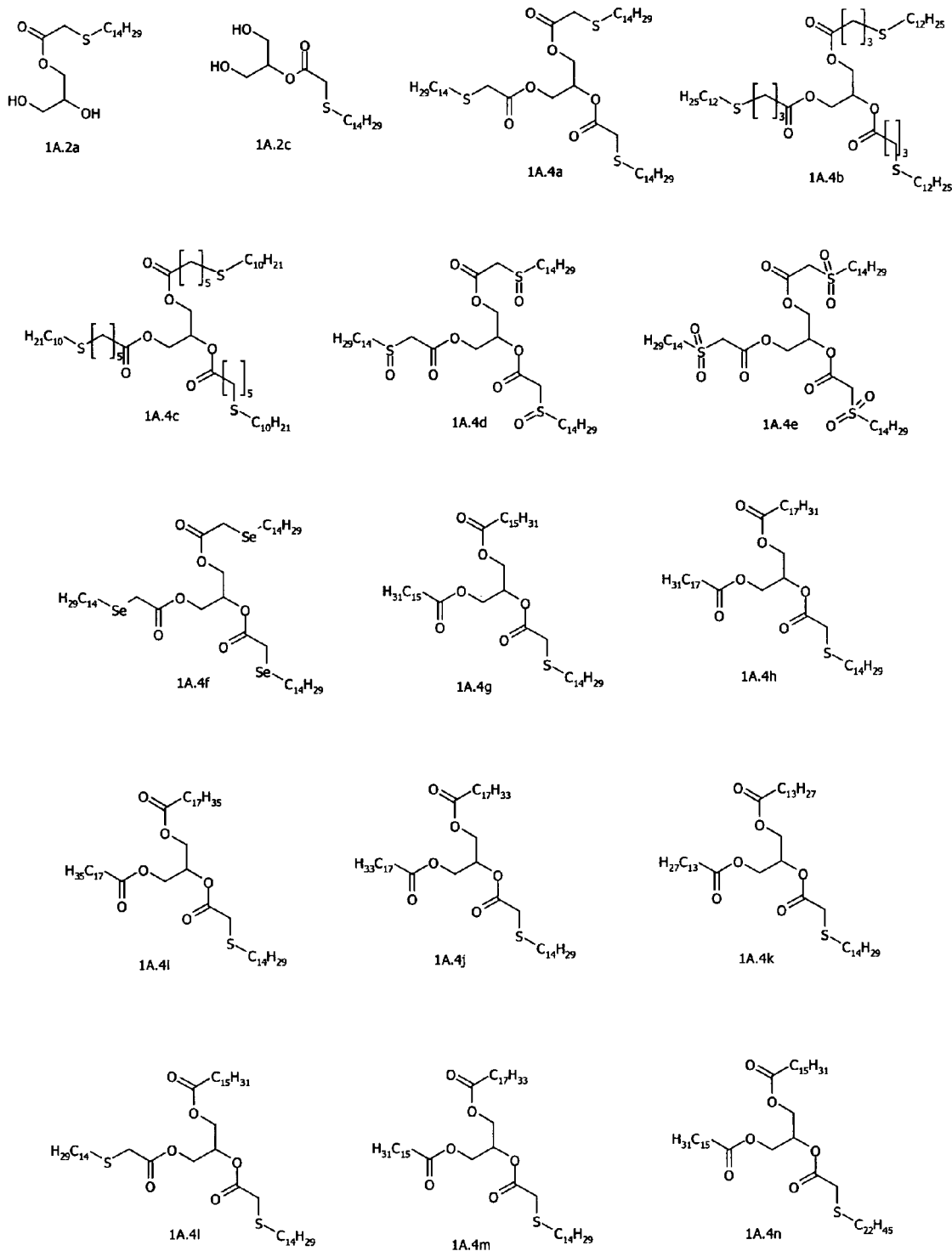

Naalsund et al., Synthesis of a triantioxidant compound: combination of β-apo-8'-carotenoic acid, selenacapryloic acid and trolox in a triglyceride, *Chemistry and Physics of Lipids*, vol. 112, 2001, pp. 59-65, XP000926796.

Database Biosis 'Online! Biosciences Information Service, Jun. 2001, Calabrese et al., Mitochondrial involvement in brain function and dysfunction: relevance to aging, neurodegenerative disorders and longevity, XP002255209.

Calabrese et al., Mitochondrial Involvement in Brain Function and Dysfunction: Relevance to Aging, Neurodegenerative Disorders and Longevity, *Neurochemical Research*, vol. 26, No. 6, 2001, pp. 739-764, XP009017939.

Markesbery et al., Oxidative Alterations in Alzheimer's Disease, *Brain Pathology*, vol. 9, No. 1, Jan. 1999, pp. 133-146, XP009007904.

Combs et al., Regulation of β-amyloid stimulated proinflammatory responses by peroxisome proliferator-activated receptor α, *Neurochemistry International*, vol. 39, 2001, pp. 449-457, XP002255208.

International Search Report of PCT/FR2004/000319, mailed Aug. 10, 2004.

Database WPI, Section Ch, Week 200036, Derwent Publications Ltd., AN 2000-328909, XP0002257696.

M.D. Rahman et al., "Effects of sulphur-containing analogues of stearic acid on growth and fatty acid biosynthesis in the protozoan crithidia-fasciculata", Journal of Medicinal Chemistry, vol. 31, No. 8, Aug. 1988, pp. 1656-1659, XP002257466, American Chemical Society.

Witten et al, Cancer, vol. 15, pp. 1041-1055, 1962.

\* cited by examiner

FATTY ACID DERIVATIVES; PREPARATION AND USES THEREOF

This application is the U.S. national phase of international application PCT/FR02/02831, filed in French on 08 Aug. 2002, which designated the U.S. PCT/FR02/02831 claims priority to FR Application No. 01 10645, filed 09 Aug. 2001. The entire contents of these applications are incorporated herein by reference.

The invention concerns novel molecules, their preparation and their uses, in particular in the field of human and veterinary medicine. The inventive compounds are partly fatty acid derivatives and exhibit advantageous pharmacological, antioxidant and anti-inflammatory properties. The invention also concerns various uses of said compounds, the pharmaceutical and cosmetic compositions containing them and methods for preparing them. The compounds of the invention are useful in particular for preventing or treating cardiovascular diseases, syndrome X, restenosis, diabetes, obesity, hypertension, certain cancers, dermatological diseases and in cosmetics, for preventing or treating the effects of skin aging, notably the appearance of wrinkles and the like.

Atherosclerosis and the cardiovascular complications thereof are the leading cause of morbidity and mortality in highly industrialized countries. Atherosclerosis and its complications are also an important consequence of type II diabetes. A clear cause-effect relationship has been demonstrated between dyslipidemias and cardiovascular diseases. Elevated levels of circulating LDL-cholesterol are unfavorable. The risk associated with high LDL-cholesterol is amplified by elevated triglyceride levels. The importance of the stability of atherosclerotic lesions in the occurrence of cardiovascular accidents has also been demonstrated. The role of LDL oxidation in the development of atherosclerotic plaque and weakening thereof is better understood.

Pharmacological treatments of atherosclerosis are aimed at lowering circulating levels of cholesterol and triglycerides, increasing the stability of atherosclerotic plaque, decreasing the mechanical constraints on the vessels (lowering blood pressure) and reducing accessory risk factors such as diabetes.

Fibrates and statins are among the medicaments currently used in the treatment of dyslipidemias. Thiazolidinediones are used in the treatment of type II diabetes.

Fibrates are widely used in the treatment of hypertriglyceridemias. They also have beneficial effects on hypercholesterolemia. Generally they are well tolerated but may cause side effects such as cutaneous reactions, neurological effects, muscle and gastrointestinal effects. Toxicities are rare (renal, muscle, joint, skin, hepatitis, etc.). Their carcinogenic potential is high in rodents but this has not been demonstrated in man.

Statins are widely used in the treatment of hypercholesterolemia. It has been shown that treating patients who have had a first vascular accident considerably reduces the risk of recurrence. Signs or symptoms of hepatitis or myopathy have been described occasionally.

Thiazolidinediones (troglitazone) have recently come into use for the treatment of insulin resistance. For this reason, post-marketing experience is insufficient to make an objective estimate of the full adverse effect profile of these drugs. In this context, the observed increase in the frequency of colon tumors in an animal model predisposed to colon cancer (Min mice with an APC gene mutation) is unfavorable. Moreover, one thiazolidinedione (troglitazone) was very recently withdrawn from the market due to problems with hepatic toxicity.

The principal drugs used for the pharmacological treatment of atherosclerosis (fibrates, statins) have a pleiotropic spectrum of action. Fibrates activate a class of nuclear receptors (PPARα, PPARγ, etc.) involved in coordinating the expression of proteins responsible for lipid transport or metabolism. The pleiotropic nature of the fibrate spectrum of action lies in the diversity of PPAR target genes. Statins reduce de novo cholesterol synthesis by inhibiting the activity of HMG-CoA reductase.

The present invention proposes a novel family of compounds exhibiting advantageous pharmacological properties useful for the preventive or curative treatment of various pathologies.

The compounds of the invention are represented by general formula (I):

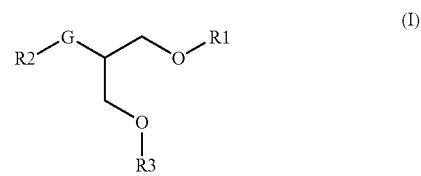

wherein:
G represents an oxygen atom, a sulfur atom or an N—R4 group in which R4 is a hydrogen atom or a linear or branched alkyl group, saturated or not, possibly substituted, containing from 1 to 5 carbon atoms,
R1, R2 and R3, which are the same or different, represent (i) a hydrogen atom, (ii) a CO—R group in which R is a linear or branched alkyl group, saturated or not, possibly substituted, the main chain of which contains from 1 to 25 carbon atoms, or (iii) a group having the formula CO—(CH$_2$)$_{2n+1}$—X—R' in which X is a sulfur atom, a selenium atom, an SO group or an SO$_2$ group, n is a whole number comprised between 0 and 11, preferably equal to 0 or 1 and even more preferably to 0, and R' is a linear or branched alkyl group, saturated or not, possibly substituted, the main chain of which contains from 13 to 23 carbon atoms and possibly one or more heterogroups, preferably 0, 1 or 2, more preferably 0 or 1, selected in the group consisting of an oxygen atom, a sulfur atom, a selenium atom, an SO group and an SO$_2$ group, at least one of the groups R1, R2 and R3 being a group having the formula CO—(CH$_2$)$_{2n+1}$—X—R' such as defined hereinabove.

The invention equally concerns a pharmaceutical composition comprising a compound represented by general formula (I).

The invention further concerns a cosmetic composition comprising a compound represented by general formula (I).

The invention also has as object the use of the hereinabove compounds as medicament, for treating various pathologies, particularly pathologies involving a deregulation of lipid metabolism.

The invention also concerns methods for preparing the compounds such as described hereinabove.

In the compounds represented by general formula (I) according to the invention, the group G advantageously represents an oxygen atom or an N—R4 group. Furthermore, when G is N—R4, R4 preferably represents a hydrogen atom or a methyl group.

In the compounds represented by general formula (I) according to the invention, the R group or groups, which are the same or different, preferably represent a linear or branched alkyl group, saturated or unsaturated, substituted or not, the main chain of which contains from 1 to 20 carbon atoms, even more preferably from 7 to 17 carbon atoms.

In the compounds represented by general formula (I) according to the invention, the R' group or groups, which are the same or different, preferably represent a linear or branched alkyl group, saturated or unsaturated, substituted or not, the main chain of which contains from 13 to 20 carbon atoms, even more preferably from 14 to 17 carbon atoms.

Specific examples of saturated long chain alkyl groups R or R' (eg., greater than or equal to 7 carbons) are in particular the groups $C_7H_{15}$, $C_{10}H_{21}$, $C_{11}H_{23}$, $C_{13}H_{27}$, $C_{14}H_{29}$, $C_{16}H_{33}$, $C_{17}H_{35}$, $C_{15}H_{31}$, $C_{20:5}(5, 8, 11, 14, 17)$ and $C_{22:6}(4, 7, 10, 13, 16, 19)$.

$C_{20:5}(5, 8, 11, 14, 17)$ is eicosapentaenoic acid (EPA) and $C_{22:6}(4, 7, 10, 13, 16, 19)$ is docosahexaenoic acid (DHA).

Examples of unsaturated long chain alkyl groups are in particular the groups $C_{14}H_{27}$, $C_{14}H_{25}$, $C_{15}H_{29}$, $C_{17}H_{29}$, $C_{17}H_{31}$, $C_{17}H_{33}$, $C_{19}H_{29}$, $C_{19}H_{31}$, $C_{21}H_{31}$, $C_{21}H_{35}$, $C_{21}H_{37}$, $C_{21}H_{39}$, $C_{23}H_{45}$.

Examples of branched long chain alkyl groups are in particular the groups $(CH_2)_{n'}$—$CH(CH_3)C_2H_5$, $(CH=C(CH_3)$—$(CH_2)_2)_{n''}$—$CH=C(CH_3)_2$ or $(CH_2)_{2x+1}$—$C(CH_3)_2$—$(CH_2)_{n'''}$—$CH_3$ (x being a whole number equal to or comprised between 1 and 11, n' being a whole number equal to or comprised between 1 and 22, n'' being a whole number equal to or comprised between 1 and 5, n''' being a whole number equal to or comprised between 0 and 22, and (2x+n''') being less than or equal to 22).

In a specific embodiment, the R group or groups, which are the same or different, may also advantageously represent a lower alkyl group containing from 1 to 6 carbon atoms. Specific examples include in particular methyl, ethyl, propyl and butyl groups, preferably methyl and ethyl.

Moreover, the alkyl group of the R or R' substituent may also be cyclic, particularly in the R group. Examples of cyclic alkyl groups are in particular cyclopropyl, cyclobutyl, cyclopentyl and cyclohexyl.

As indicated hereinabove, the alkyl groups may optionally be substituted by one or more substituents, which are the same or different. The substituents are preferably selected in the group consisting of a halogen atom (iodine, chlorine, fluorine, bromine) and an OH, =O, $NO_2$, $NH_2$, CN, $CH_2$—O, $CH_2OCH_3$, $CF_3$ or COOZ group (Z being a hydrogen atom or an alkyl group, preferably containing from 1 to 6 carbon atoms).

In a compound represented by general formula (I), the R and R' alkyl groups may be the same or different. However, preferred compounds are those wherein the R' alkyl groups are the same or have a similar chain length, that is to say, differing by not more than approximately 3 carbon atoms.

An especially preferred example of an R' group is a saturated and linear alkyl group, advantageously containing from 13 to 17 carbon atoms, preferably from 14 to 16, even more preferably 14 atoms.

Moreover, in the group CO—$(CH_2)_{2n+1}$—X—R', X most preferably represents represents a sulfur or selenium atom and advantageously a sulfur atom.

Moreover, in the group CO—$(CH_2)_{2n+1}$—X—R', n is preferably different from 1 and in particular is equal to 0.

A specific example of CO—$(CH_2)_{2n+1}$—X—R' group according to the invention is the group CO—$CH_2$—S—$C_{14}H_{29}$.

Preferred compounds of the invention are therefore compounds having general formula (I) hereinabove wherein at least one of the groups R1, R2 and R3 represents a CO—$(CH_2)_{2n+1}$—X—R' group in which X represents a selenium atom or preferably a sulfur atom and/or R' is a saturated and linear alkyl group containing from 13 to 17 carbon atoms, preferably from 14 to 16, even more preferably 14 carbon atoms.

In this respect, specific inventive compounds are those wherein R2 is a group having the formula CO—$(CH_2)_{2n+1}$—X—R', preferably in which X represents a selenium atom or preferably a sulfur atom and/or R' is a saturated and linear alkyl group containing from 13 to 17 carbon atoms, more preferably in which n is equal to 0, in particular a group having the formula CO—$CH_2$—S—$C_{14}H_{29}$.

In said compounds, R1 and R3, which are the same or different, advantageously represent a hydrogen atom or a CO—R group, preferably a CO—R group.

Other specific inventive compounds are those in which two of the groups R1, R2 and R3 are CO—$(CH_2)_{2n+1}$—X—R' groups, which are the same or different, preferably in which X represents a selenium atom or preferably a sulfur atom and/or R' is a saturated and linear alkyl group containing from 13 to 17 carbon atoms, more preferably in which n is equal to 0, in particular a group having the formula CO—$CH_2$—S—$C_{14}H_{29}$.

Especially preferred compounds are compounds represented by general formula (I) hereinabove wherein:
G is an N—R4 group in which R4 is a hydrogen atom or a methyl group, and
at least two of the groups R1, R2 and R3 represent a CO—$(CH_2)_{2n+1}$—X—R' group such as defined hereinabove, which is the same or different, preferably the same.

Other preferred compounds are compounds represented by general formula (I) hereinabove wherein R1, R2 and R3, which are the same or different, preferably the same, represent a CO—$(CH_2)_{2n+1}$—X—R' group such as defined hereinabove, preferably in which X represents a selenium atom or preferably a sulfur atom and/or R' is a saturated and linear alkyl group containing from 13 to 17 carbon atoms, more preferably in which n is equal to 0, and in particular CO—$CH_2$—S—$C_{14}H_{29}$ groups.

Another family of preferred compounds comprises compounds having general formula (I) hereinabove in which one of the groups R1, R2 and R3 is a CO—$(CH_2)_{2n+1}$—X—R' groups such as defined hereinabove, another of the groups R1, R2 and R3 is a CO—R group such as defined hereinabove and the third of the groups R1, R2 and R3 is a hydrogen atom.

A particular family is that wherein R1 is a group having formula CO—$(CH_2)_{2n+1}$—X—R', preferably in which X represents a selenium atom or preferably a sulfur atom and/or R' is a saturated and linear alkyl group containing from 13 to 17 carbon atoms, more preferably in which n is equal to 0 and in particular a CO—$CH_2$—S—$C_{14}H_{29}$ group. In said family, one and/or both groups R2 and R3 advantageously represent a hydrogen atom or preferably a CO—R group, which is the same or different.

Another family of inventive compounds is that wherein one of the groups R1, R2 or R3 is a $COCH_3$ group.

Preferred compounds in the scope of the invention are those represented by general formula (I) hereinabove, in which:
R2 is a group having the formula CO—$(CH_2)_{2n+1}$—X—R', in particular CO—$CH_2$—S—$C_{14}H_{29}$ and, preferably, R1 and R3, which are the same or different, represent a hydrogen atom or a CO—R group. Said compounds in which R1 and R3, which are the same or different, both represent a CO—R group are preferred; or R1 is a group having the formula CO—$(CH_2)_{2n+1}$—X—R', in particular a CO—$CH_2$—S—$C_{14}H_{29}$ group and, preferably, one and/or both groups R2 and R3 represent a hydrogen atom or a CO—R group, the same or different; or R1, R2, and R3, which are the same, represent a group having the formula CO—$(CH_2)_{2n+1}$—X—R', in particular CO—$CH_2$—S—$C_{14}H_{29}$.

Figure 1B:
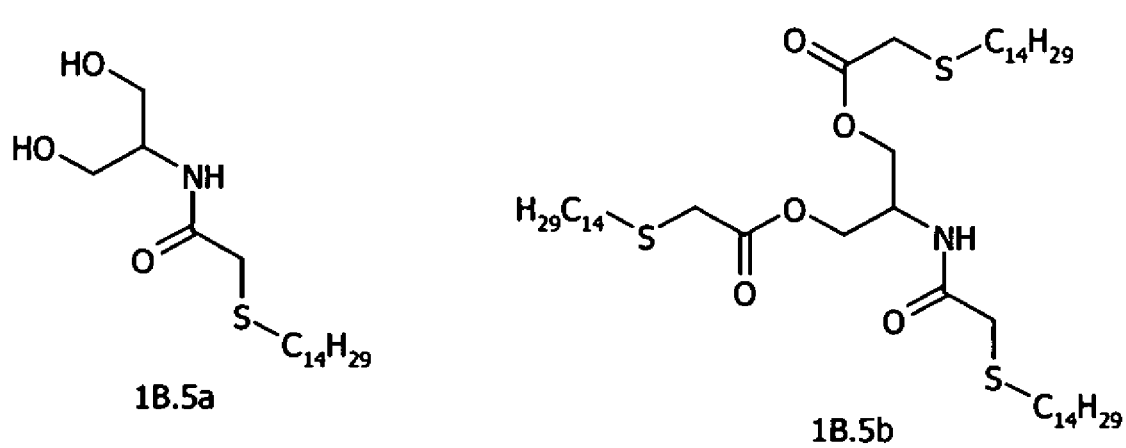

Examples of preferred compounds according to the invention are shown in FIGS. 1A and 1B.

The inventive compounds may be in the form of salts, particular basic or acid addition salts, preferably compatible with pharmaceutical or cosmetic use. Non-limiting examples of pharmaceutically or cosmetically acceptable acids include hydrochloric, hydrobromic, sulfuric, phosphoric, acetic, trifluoroacetic, lactic, pyruvic, malonic, succinic, glutaric, fumaric, tartaric, maleic, citric, ascorbic, camphoric acids, etc. Non-limiting examples of pharmaceutically or cosmetically acceptable bases include sodium hydroxide, potassium hydroxide, triethylamine, tert-butylamine, etc.

The invention also concerns the use of compounds represented by general formula (I) and in particular those described hereinabove, in the field of pharmaceutics or cosmetics.

It thus concerns the use of a compound represented by general formula (I) and in particular such as described hereinabove for preparing a pharmaceutical composition for preventing and/or treating various pathologies, such as in particular cardiovascular diseases, syndrome X, restenosis, diabetes, obesity, hypertension, cancer or dermatological diseases. It further concerns the use of a compound represented by general formula (I) and in particular such as described hereinabove for preparing a cosmetic composition for protecting the skin, for fighting against skin aging and its effects, for fighting against the appearance or development of wrinkles, and the like.

Thus, the compounds useful in the pharmaceutical or cosmetic field are represented by general formula (I) in which:

G represents an oxygen atom, a sulfur atom or an N—R4 group in which R4 is a hydrogen atom or a linear or branched alkyl group, saturated or not, possibly substituted, containing from 1 to 5 carbon atoms, R1, R2 and R3, which are the same or different, represent (i) a hydrogen atom, (ii) a CO—R group in which R is a linear or branched alkyl group, saturated or not, possibly substituted, the main chain of which contains from 1 to 25 carbon atoms, or (iii) a group having the formula CO—$(CH_2)_{2n+1}$—X—R' in which X is a sulfur atom, a selenium atom, an SO group or an $SO_2$ group, n is a whole number comprised between 0 and 11, preferably equal to 0 or 1 and even more preferably to 0, and R' is a linear or branched alkyl group, saturated or not, possibly substituted, the main chain of which contains from 2 to 23 carbon atoms and possibly one or more heterogroups, preferably 0, 1 or 2, more preferably 0 or 1, selected in the group consisting of an oxygen atom, a sulfur atom, a selenium atom, an SO group or an $SO_2$ group, at least one of the groups R1, R2 and R3 being a group having the formula CO—$(CH_2)_{2n+1}$—X—R' such as defined hereinabove.

In this respect the preferred compounds used correspond to compounds having formula (I) wherein R' is a linear or branched alkyl group, saturated or not, possibly substituted, the main chain of which contains from 9 to 23 carbon atoms and possibly one or more heterogroups. In an advantageous manner, the compounds having formula (I) which are used are such as defined hereinabove.

The use of an inventive compound may in fact allow to lower circulating levels of triglycerides and cholesterol, inhibit the oxidative modification of LDL, induce the expression of enzymes involved in mitochondrial and peroxisomal β-oxidation, increase the oxidation capacities of hepatic fatty acids, induce mitochondrial growth in type I and II muscle fibers, activate PPARα and PPARγ, or else reduce tumor cell growth.

In this respect, the inventive compounds advantageously exhibit an improved tropism for liver and may therefore be administered by the oral or systemic route. Moreover, by virtue of their structure, the inventive compounds have a long-lasting effect.

The invention is aimed at developing a pharmaceutical composition comprising at least one inventive compound possibly combined with a pharmaceutically acceptable vehicle.

The invention also concerns a cosmetic composition comprising at least one inventive compound possibly combined with a cosmetically acceptable vehicle.

The invention further concerns a nutritional composition containing at least one of the compounds such as defined hereinabove, which may be used alone or in combination with other agents.

The invention also concerns a treatment method comprising administering to a mammal an efficient amount of a compound according to the invention. The mammals concerned may be animals, domestic or otherwise, or human beings.

The compounds or compositions of the invention may be administered in different ways and in different forms. For instance, they may be administered systemically, by the oral route, parentally, by inhalation or by injection, such as for example by the intravenous, intramuscular, subcutaneous, transdermal, intra-arterial route, etc. For injections, the compounds are generally prepared in the form of liquid suspensions, which may be injected through syringes or by infusion, for instance. In this respect, the compounds are generally dissolved in pharmaceutically compatible saline, physiologic, isotonic, buffered solutions and the like, known to those skilled in the art. For instance, the compositions may contain one or more agents or vehicles selected from among dispersives, solubilizers, emulsifiers, stabilizers, preservatives, buffers, and the like. Agents or vehicles that may be used in the liquid and/or injectable formulations comprise in particular methylcellulose, hydroxymethylcellulose, carboxymethylcellulose, polysorbate 80, mannitol, gelatin, lactose, vegetable oils, acacia, liposomes, and the like.

The compounds may thus be administered in the form of gels, oils, tablets, suppositories, powders, gelatin capsules, capsules, aerosols, and the like, possibly by means of pharmaceutical forms or devices allowing sustained and/or delayed release. For this type of formulation, an agent such as cellulose, carbonates or starches is advantageously used.

The compounds may be administered orally in which case the agents or vehicles used are preferably selected from among water, gelatin, gums, lactose, starch, magnesium stearate, talc, an oil, polyalkylene glycol, and the like.

For parenteral administration, the compounds are preferably administered as solutions, suspensions or emulsions, in particular with water, oil or polyalkylene glycols to which, in addition to preservatives, stabilizers, emulsifiers, etc., it is possible to also add salts to adjust osmotic pressure, buffers, and the like.

For a cosmetic use, the inventive compounds may be administered in the form of creams, such as for example skin care creams, sun creams, oils, gels and the like.

It is understood that the injection rate and/or injected dose may be adapted by those skilled in the art according to the patient, the pathology, the mode of administration, etc. Typically, the compounds are administered at doses ranging from 1 µg to 2 g per dose, preferably from 0.1 mg to 1 g per administration. The doses may be administered once a day or several times a day, as the case may be. Moreover, the compositions of the invention may also comprise other active substances or agents.

The compounds of the invention may be prepared from commercially available products, employing a combination of chemical reactions known to those skilled in the art. The invention also concerns methods for preparing the hereinabove compounds.

According to a first method of the invention, the compounds represented by formula (I) in which G is an oxygen or sulfur atom, R1, R2 and R3, which are the same or different, represent a CO—R group or a CO—$(CH_2)_{2n+1}$—X—R' group, are obtained from a compound having formula (I) in which G is respectively an oxygen or sulfur atom, R2 is a hydrogen atom and R1 and R3, which are the same or different, represent a CO—R or CO—$(CH_2)_{2n+1}$—X—R' group, and a compound having the formula A°-CO-A in which A is a reactive group selected for example in the group consisting of OH, Cl, O—CO-A° and OR", R" being an alkyl group, and A° is the R group or $(CH_2)_{2n+1}$—X—R' group, possibly in the presence of coupling agents or activators known to those skilled in the art.

The compounds represented by formula (I) according to the invention in which G is an oxygen atom, R2 is a hydrogen atom and R1 and R3, which are the same or different, represent a CO—R or CO—$(CH_2)_{2n+1}$—X—R' group, may be obtained in different ways.

In a first embodiment, a glycerol molecule is reacted with a compound having the formula A°-CO-A1 in which A1 is a reactive group selected for example in the group consisting of OH, Cl and OR", R" being an alkyl group, and A° is the R group or the $(CH_2)_{2n+1}$—X—R' group, possibly in the presence of coupling agents or activators known to those skilled in the art. Said reaction enables the synthesis of so-called symmetrical compounds, in which R1 and R3 have the same definition. Said reaction may be carried out by adapting the protocols described for example in Feuge et al., J. Am. Oil Chem. Soc., 1953, 30, 320-325; Gangadhar et al., Synth. Commun., 1989, 19, 2505-2514; Han et al., Biorg. Med. Chem. Lett., 1999, 9, 59-64; or Robinson, J. Pharm. Pharmacol., 1960, 12, 685-689.

The compounds represented by formula (I) according to the invention in which G is an oxygen atom, R2 is a hydrogen atom and R1 and R3, which are the same or different, represent a CO—R or CO—$(CH_2)_{2n+1}$—X—R' group, may also be obtained from a compound having formula (I) according to the invention in which G is an oxygen atom, R2 and R3 representent a hydrogen atom and R1 is a CO—R or CO—$(CH_2)_{2n+1}$—X—R' group (this particular form of formula (I) compounds being named compounds IV), and a compound having the formula A°-CO-A2 in which A2 is a reactive group selected for example in the group consisting of OH and Cl, and A° is the R group or the $(CH_2)_{2n+1}$—X—R' group, possibly in the presence of coupling agents or activators known to those skilled in the art. Said reaction is advantageously carried out according to the protocol described for example in Daubert et al., J. Am. Chem. Soc., 1943, 65, 2144-2145; Feuge and Lovegren, J. Am. Oil Chem. Soc., 1956, 33, 367-372; Katoch et al., Bioorg. Med. Chem., 1999, 7, 2753-2758 or Strawn et al., J. Med. Chem., 1989, 32, 643-648.

Compounds IV described hereinabove may be prepared by a method comprising:

a) reacting a compound represented by general formula (II)

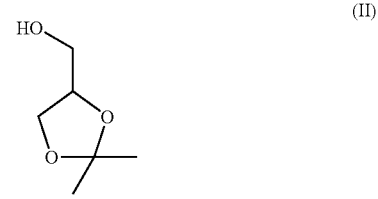

with a compound having the formula A°-CO-A2 in which A2 is a reactive group selected for example in the group consisting of OH and Cl, and A° is the R group or the $(CH_2)_{2n+1}$—X—R' group, possibly in the presence of coupling agents or activators known to those skilled in the art, to give a compound represented by general formula (III)

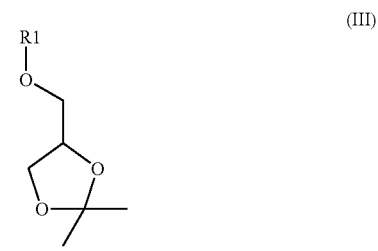

in which R1 represents a CO—R or CO—$(CH_2)_{2n+1}$—X—R' group; and b) deprotecting the compound (III) by an acid (acetic acid, trifluoroacetic acid, boric acid, sulfuric acid, etc.) to give a compound having general formula (IV) as defined hereinabove.

According to another particular method of the invention, compounds represented by formula (I) in which G is an oxygen atom, R3 is a hydrogen atom and R1 and R2, which are the same or different, represent a CO—R or CO—$(CH_2)_{2n+1}$—X—R' group, may be obtained from a compound having formula (I) according to the invention in which G is an oxygen atom, R2 and R3 represent a hydrogen atom and R1 is a CO—R or CO—$(CH_2)_{2n+1}$—X—R' group (compounds IV), according to the following steps:

a) reacting compound (IV) with a compound PxE wherein Px is a protecting group; and E is a reactive group selected for example in the group consisting of OH and a halogen, to give a compound having general formula (V) in which R1 is a CO—R or CO—$(CH_2)_{2n+1}$—X—R' group. Advantageously, the reaction may be carried out by adapting the method described by Gaffney and Reese, Tet. Lett., 1997, 38, 2539-2542 in which PxE can represent the compound 9-phenylxanthene-9-ol or 9-chloro-9-phenylxanthene

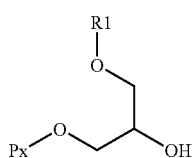

(V)

b) reacting the compound having formula (V) with a compound having the formula A°-CO-A2 in which A2 is a reactive group selected for example in the group consisting of OH and Cl, and A° is the R group or the $(CH_2)_{2n+1}$—X—R' group, possibly in the presence of coupling agents or activators known to those skilled in the art, to give a compound corresponding to general formula (VI), in which R1 and R2, which are the same or different, represent a CO—R or CO—$(CH_2)_{2n+1}$—X—R' group and Px is a protecting group

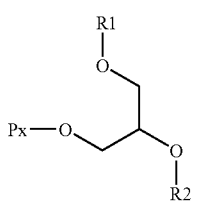

(VI)

c) deprotecting the compound (VI), in acidic medium to give a compound represented by general formula (I) in which G is an oxygen atom, R3 is a hydrogen atom and R1 and R2, which are the same or different, represent a CO—R or CO—$(CH_2)_{2n+1}$—X—R' group.

In another specific inventive method, the compounds represented by general formula (I) in which G is an oxygen atom, R1 and R3 represent a hydrogen atom and R2 represents a CO—R or CO—$(CH_2)_{2n+1}$—X—R' group, are obtained by a method comprising:

a) reacting a compound represented by formula (VII)

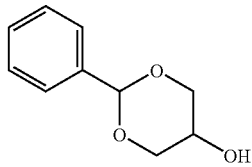

(VII)

with a compound having the formula A°-CO-A2 in which A2 is a reactive group selected for example in the group consisting of OH and Cl, and A° is the R group or the $(CH_2)_{2n+1}$—X—R' group, possibly in the presence of coupling agents or activators known to those skilled in the art, to give a compound represented by general formula (VIII)

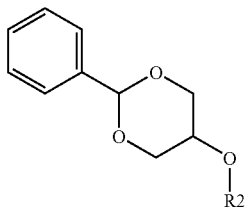

(VIII)

in which R2 represents a CO—R or CO—$(CH_2)_{2n+1}$—X—R' group; and b) deprotecting the compound represented by formula (VIII) in acidic medium or by catalytic hydrogenation to give a compound having general formula (I) in which G is an oxygen atom, R1 and R3 represent a hydrogen atom and R2 represents a CO—R or CO—$(CH_2)_{2n+1}$—X—R' group In an advantageous manner, the hereinabove steps may be carried out according to the protocols described in Bodai et al., *Syn. Lett.*, 1999, 6,759-761; Paris et al., *J. Med. Chem.*, 1980, 23, 9-12; Scriba et al., *Arch. Pharm.* (Weinheim), 1993, 326, 477-481 or Seltzman et al., *Tet. Lett.*, 2000, 41, 3589-3592.

Compounds represented by formula (I) according to the invention in which G is a sulfur atom, R2 is a hydrogen atom and R1 and R3, which are the same or different, represent a CO—R or CO—$(CH_2)_{2n+1}$—X—R' group, may be obtained from a compound represented by formula (IX) by the following method:

(IX)

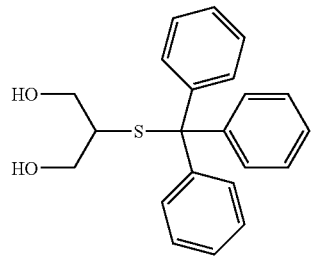

a) reacting the compound (IX) and a first compound having the formula A°-CO-A3 in which A3 is a reactive group selected for example in the group consisting of OH, O—CO-A° and Cl, and A° is the R group or the $(CH_2)_{2n+1}$—X—R' group, then a second compound having the formula A°-CO-A3 in which, independently of the first compound, A3 is a reactive group selected for example in the group consisting of OH, O—CO-A° and Cl, and A° is the R group or the $(CH_2)_{2n+1}$—X—R' group, possibly in the presence of coupling agents or activators known to those skilled in the art, b) deprotecting the thiol group by mercuric acetate.

Said method is advantageously executed according to the protocol described in Aveta et al., *Gazz. Chim. Ital.*, 1986, 116 (11), 649-652.

Compounds represented by formula (I) according to the invention in which G is a sulfur atom, R2 and R3 are hydrogen atoms and R1 represents a CO—R or CO—$(CH_2)_{2n+1}$—X—R' group, may be obtained from a compound represented by formula (IX) by the following method:

a) reacting the compound (IX) with a first compound having the formula A°-CO-A3 in which A3 is a reactive group selected for example in the group consisting of OH, O—CO-A° and Cl, and A° is the R group or the $(CH_2)_{2n+1}$—X—R' group in stoichiometric quantity, possibly in the presence of coupling agents or activators known to those skilled in the art, b) deprotecting the thiol group by mercuric acetate.

The compound represented by formula (IX) may be prepared by a method comprising:

a) reacting a dimethyl 2-halogenomalonate with tritylthiol to give a compound represented by formula (X)

(X)

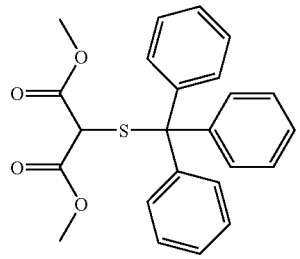

b) reducing the acetate functions with LiAlH$_4$.

Compounds represented by formula (I) in which G is an N—R4 group and in which R1, R2 and R3, which are the same or different, represent a CO—R group or a CO—(CH$_2$)$_{2n+1}$—X—R' group, are obtained from a compound represented by formula (I) in which G is an N—R4 group, R1 and R3 are hydrogen atoms, R2 is a CO—R group or a CO—(CH$_2$)$_{2n+1}$—X—R' group (compound XI) according to the following method:

Reacting a compound (XI) and a first compound having the formula A°-CO-A2 in which A2 is a reactive group selected for example in the group consisting of OH and Cl, and A° is the R group or the (CH$_2$)$_{2n+1}$—X—R' group, then with a second compound having the formula A°-CO-A2 in which, independently of the first compound, A2 is a reactive group selected for example in the group consisting of OH and Cl, and A° is the R group or the (CH$_2$)$_{2n+1}$—X—R' group, possibly in the presence of coupling agents or activators known to those skilled in the art.

Said method is advantageously carried out according to the protocol described in Terradas et al., *J. Amer. Chem. Soc.*, 1993, 115, 390-396.

Compounds represented by formula (I) according to the invention in which G is an N—R4 group and in which R1 and R2 represent a CO—R or CO—(CH$_2$)$_{2n+1}$—X—R' group, and R3 is a hydrogen atom may be obtained by reacting a compound (XI) and a compound having the formula A°-CO-A2 in which A2 is a reactive group selected for example between OH and Cl, and A° is the R group or the (CH$_2$)$_{2n+1}$—X—R' group in stoichiometric quantity, possibly in the presence of coupling agents or activators known to those skilled in the art.

Compounds represented by formula (I) according to the invention in which G is an NH group, R1 and R3 are hydrogen atoms, R2 is a CO—R group or a CO—(CH$_2$)$_{2n+1}$—X—R' group (compound XIa), may be obtained in different ways.

In a first method, a molecule of 2-aminopropane-1,3-diol is reacted with a compound having the formula A°-CO-A in which A is a reactive group selected for example in the group consisting of OH, O—CO-A°, OR" and Cl, and A° is the R group or the (CH$_2$)$_{2n+1}$—X—R' group, possibly in the presence of coupling agents or activators known to those skilled in the art.

Said reaction may be carried out by adapting the protocols described for example in Daniher and Bashkin, *Chem. Commun.*, 1998, 10, 1077-1078; Khanolkar et al., *J. Med. Chem.*, 1996, 39, 4515-4519; Harada et al., *Chem. Pharm. Bull.*, 1996, 44 (12), 2205-2212; Kurfuerst et al., *Tetrahedron*, 1993, 49 (32), 6975-6990; Shaban et al., *Carbohydr. Res.*, 1977, 59, 213-233; Putnam and Bashkin, Chem. Commun., 2000, 767-768.

Compounds represented by formula (I) according to the invention in which G is an NH group, R1 and R3 are hydrogen atoms, R2 is a CO—R group or a CO—(CH$_2$)$_{2n+1}$—X—R' group (compound XIa) may also be obtained by the following method:

a) reacting a compound represented by formula (XII) with a compound having the formula A°-CO-A in which A is a reactive group selected for example in the group consisting of OH, O—CO-A°, OR" and Cl, and A° is the R group or the (CH$_2$)$_{2n+1}$—X—R' group, possibly in the presence of coupling agents or activators known to those skilled in the art

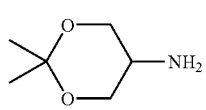

(XII)

to give a compound represented by general formula (XIII)

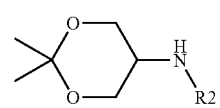

(XIII)

b) deprotecting the compound (XIII).

Said method is advantageously carried out according to the protocol described in Harada et al., *Chem. Pharm. Bull.*, 1996, 44 (12), 2205-2212.

Compounds represented by formula (I) according to the invention in which G is an N—R4 group in which R4 is not a hydrogen atom, R1 and R3 are hydrogen atoms, R2 is a CO—R group or a CO—(CH$_2$)$_{2n+1}$—X—R' group (compound XIb) may be obtained according to the following method:

a) reacting a compound having formula (XII) with a compound having the formula A°-CO-A in which A is a reactive group selected for example in the group consisting of OH, O—CO-A°, OR" and Cl, and A° is the R group or the (CH$_2$)$_{2n+1}$—X—R' group, possibly in the presence of coupling agents or activators known to those skilled in the art.

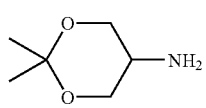

(XII)

to give a compound represented by general formula (XIII)

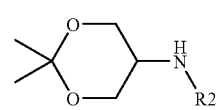

(XIII)

b) reacting the compound XII with a compound of the type R4-A4 in which A4 is a reactive group selected for example in the group consisting of Cl or Br, in basic medium, c) deprotecting the compound XIII.

The feasibility, realization and other advantages of the invention will become apparent in the following examples, which are given for purposes of illustration and not by way of limitation.

LEGENDS OF FIGURES

FIG. 1A: Structure of acylglycerols according to the invention (examples 2a, 2c, 4a-n).

FIG. 1B: Structure of particular compounds according to the invention (examples 5a-b).

Figure 2:
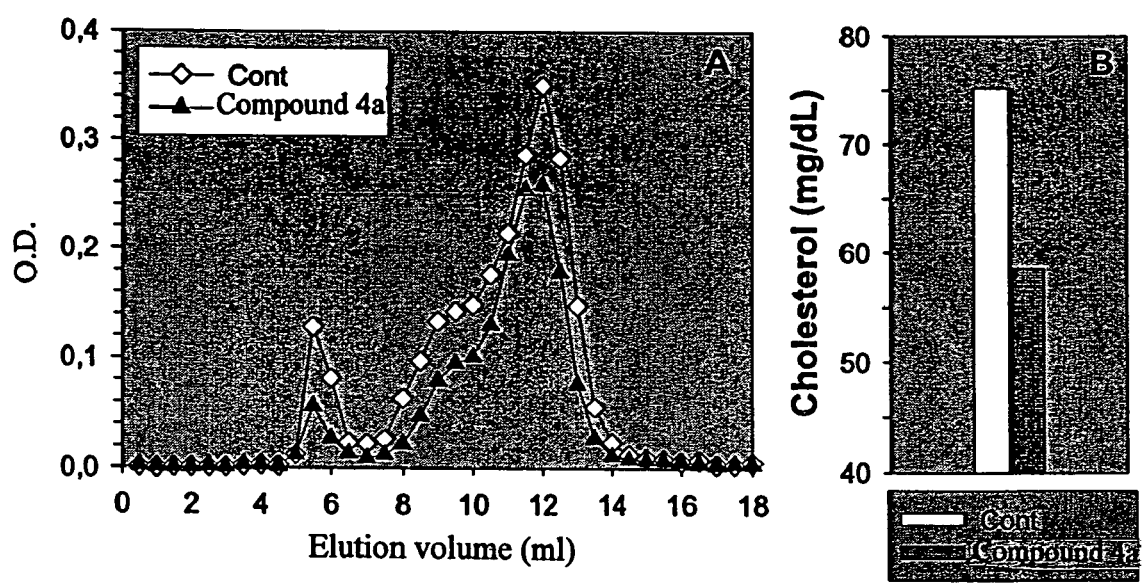

FIG. 2: Evaluation of the effects of compound 4a on plasma cholesterol metabolism in the rat.

FIG. 2A shows the effects of treating Sprague-Dawley rats with the compound of example 4a (300 mg/kg/d) on cholesterol distribution in lipoparticles as evaluated by size exclusion chromatography. Cholesterol showed a typical distribution in several lipoparticles classes of different size. A decrease in cholesterol in the different lipoparticle classes was seen after treating the animals with the compound of example 4a, particularly in large particles (VLDL) and small particles (HDL). This decrease is characteristic of the effects of PPARα activators.

This decrease resulted in a reduction of total plasma cholesterol levels as shown in FIG. 2B.

Figure 3:
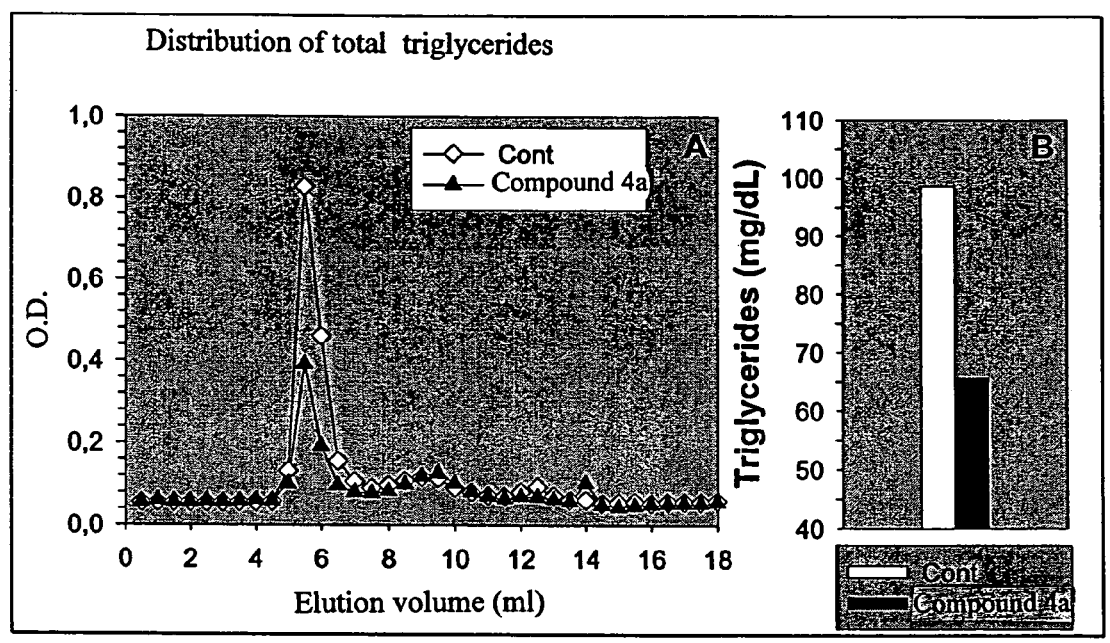

FIG. 3: Evaluation of the effects of compound 4a on plasma triglyceride metabolism in the rat.

FIG. 3A shows the effects of treating Sprague-Dawley rats with the compound of example 4a (300 mg/kg/d) on triglyceride distribution in lipoparticles as evaluated by size exclusion chromatography. Triglycerides were typically distributed mainly in the large lipoparticle class. A decrease in triglycerides in this lipoparticle class was seen after treating the animals with the compound of example 4a. This decrease is characteristic of the effects of PPARα activators. This decrease resulted in a reduction of plasma triglyceride levels as shown in 3B.

Figure 4:
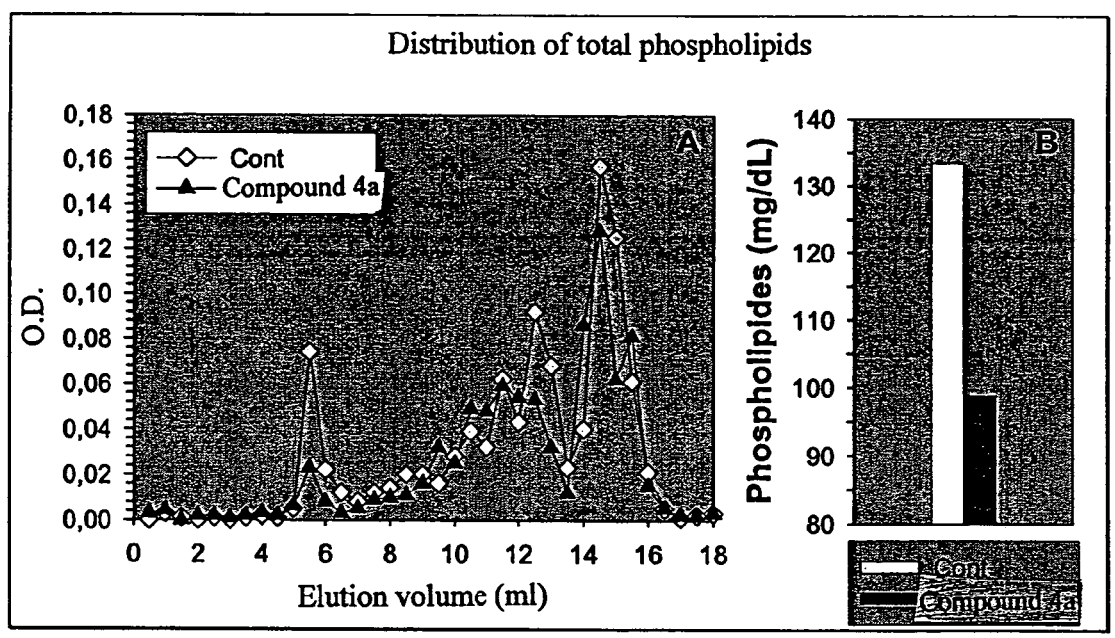

FIG. 4: Evaluation of the effects of compound 4a on plasma phospholipid metabolism in the rat.

FIG. 4A shows the effects of treating Sprague-Dawley rats with the compound of example 4a (300 mg/kg/d) on phospholipid distribution in lipoparticles as evaluated by size exclusion chromatography. A typical distribution of phospholipids was observed in several lipoparticle classes of different size. A decrease in phospholipids in the different lipoparticle classes was seen after treating the animals with the compound of example 4a, particularly in large particles (VLDL).

This decrease resulted in a reduction of total plasma phospholipid levels as shown in FIG. 4B.

Figure 5:
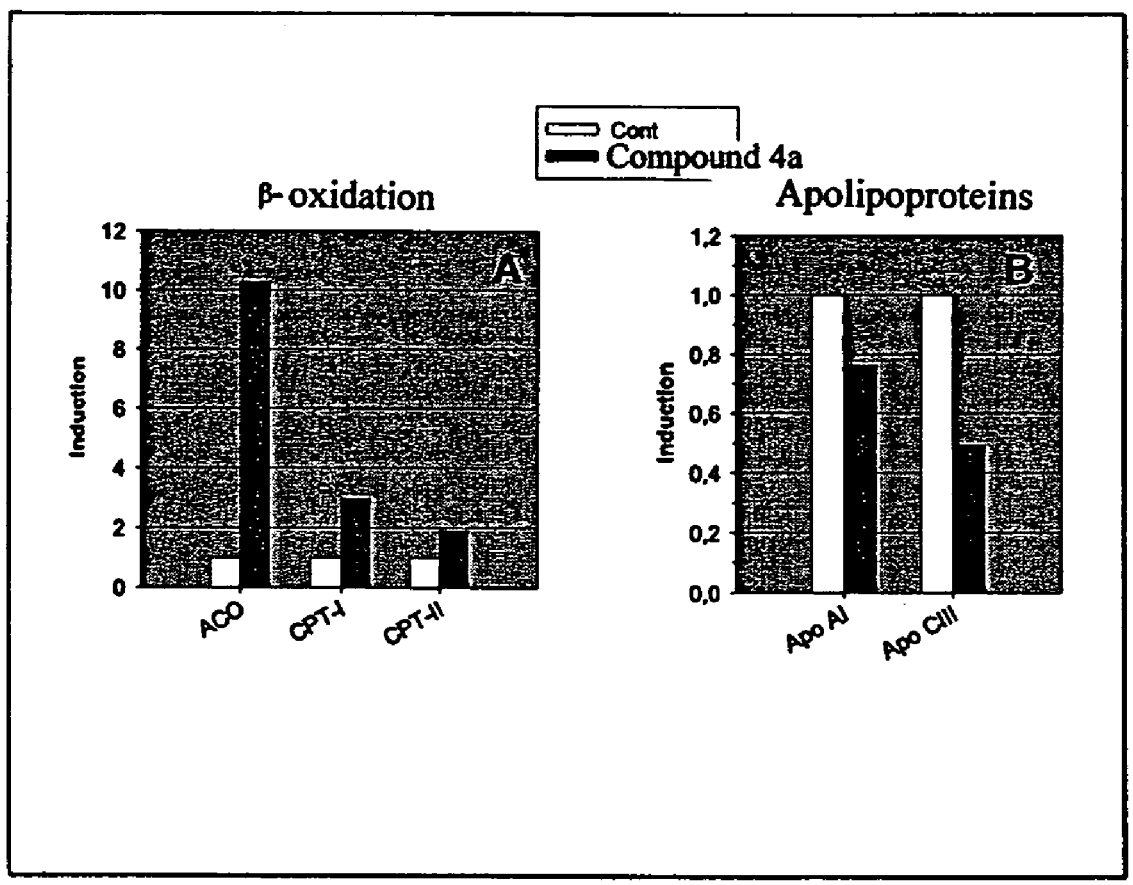

FIG. 5: Evaluation of the effects of compound 4a on the expression of hepatic genes in the rat.

FIG. 5A shows the effects of treating Sprague-Dawley rats with the compound of example 4a (300 mg/kg/d) on hepatic expression of genes involved in peroxisomal (ACO) or mitochondrial (CPT-I and CPT-II) β-oxidation of fatty acids. A strong activation of hepatic expression of ACO, one of the main target genes of PPARα, was observed, suggesting a strong activation of fatty acid catabolic capacity by liver peroxisomes. At the same time, there was a smaller increase in the expression of the genes CPT-I and CPT-II, suggesting an activation of fatty acid catabolic capacity by liver mitochondria.

FIG. 5B shows the effects of treating Sprague-Dawley with the compound of example 4a (300 mg/kg/d) on hepatic expression of genes involved in transport of cholesterol (Apo AI) or triglycerides (Apo CIII). A slight decrease in hepatic Apo AI expression was observed, which might partly explain the decrease in plasma cholesterol levels. There was also a more marked decrease in Apo CIII expression which might partly explain the decrease in plasma triglycerides.

Figure 6:
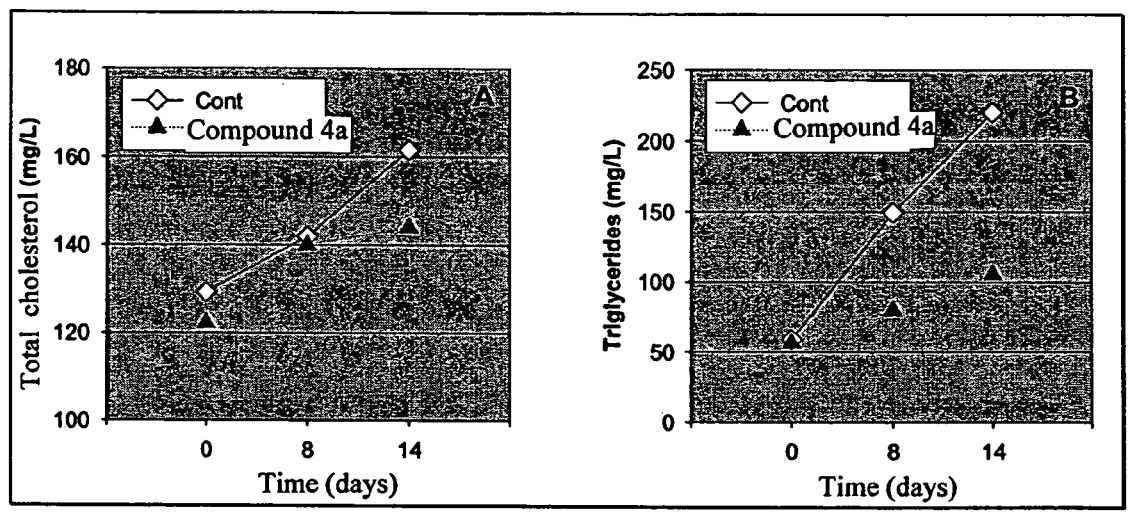

FIG. 6: Evaluation of the effects of compound 4a on plasma cholesterol and triglyceride metabolism in Zucker rats.

FIG. 6A shows the effects of treating Zucker rats with the compound of example 4a (300 mg/kg/d) on total plasma cholesterol. Zucker rats are insulin-resistant and are characterized by a gradual increase in plasma cholesterol. FIG. 1a illustrates this increase in the control group. It also shows that said increase was slower after treating the animals with the compound of example 4a. FIG. 6A shows the effects of treating Zucker rats with the compound of example 4a (300 mg/kg/d) on plasma triglycerides. Zucker rats also exhibit a gradual increase in plasma triglycerides. FIG. 6B illustrates this increase in the control group. It also shows that said increase was markedly slower after treating the animals with the compound of example 4a.

Figure 7:
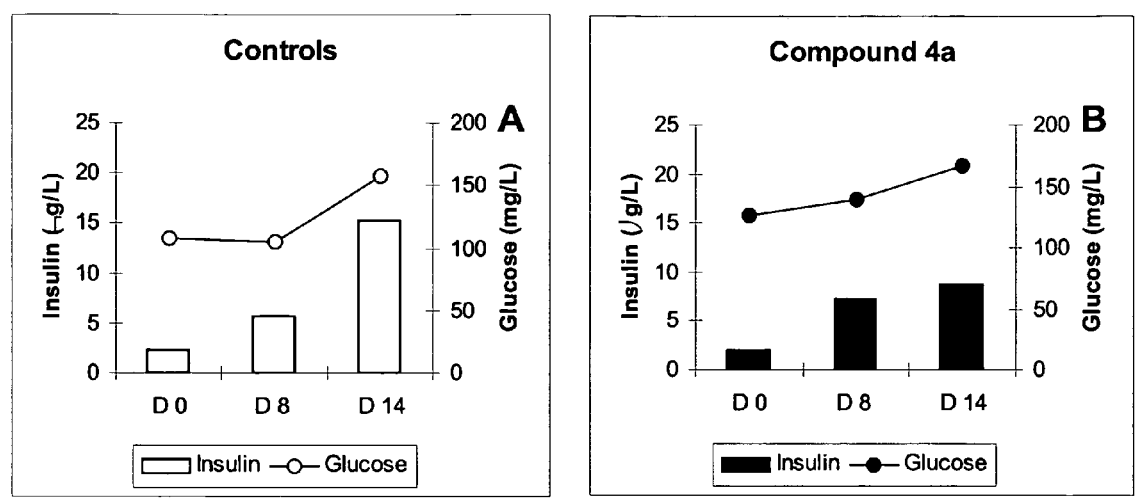

FIG. 7: Evaluation of the effects of compound 4a on plasma insulin and glucose balance in Zucker rats.

FIG. 7 shows the effects of treating Zucker rats with the compound of example 4a (300 mg/kg/d) on plasma insulin and glucose. Zucker rats are insulin-resistant and show a gradual compensatory increase in plasma insulin levels. FIG. 7a illustrates this increase in the control group. FIG. 7B shows that said increase was slower after treating the animals with the compound of example 4a, especially after 14 days. As glucose levels were equivalent in the two groups (FIGS. 7A and 7B), treatment with the compound of example 4a therefore increased insulin sensitivity.

Figure 8:
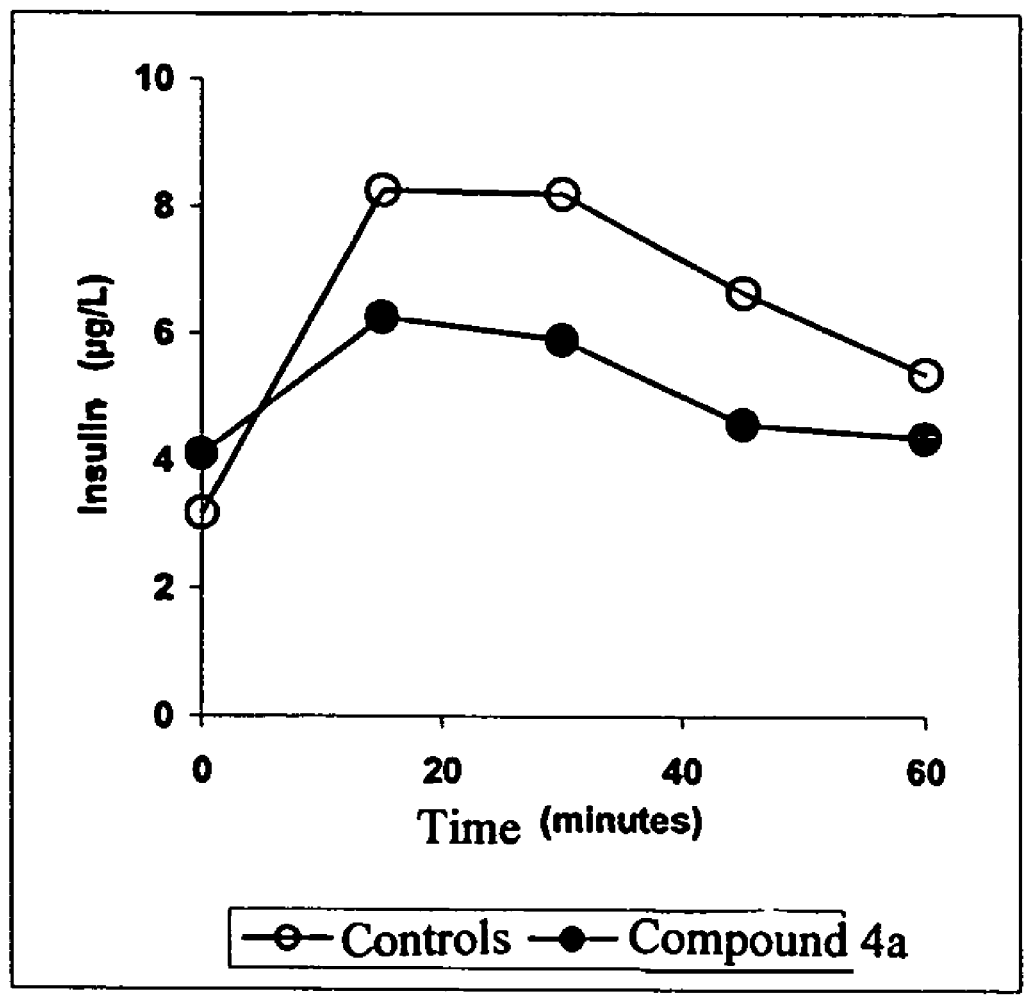

FIG. 8: Evaluation of the effects of compound 4a on insulin levels during a glucose tolerance test in Zucker rats.

FIG. 8 shows the effects of treating Zucker rats with the compound of example 4a (300 mg/kg/d) on plasma insulin levels during a glucose tolerance test. The results show that rats treated with compound 4a used less insulin in response to the glucose injection at the start of the test. Treatment with the compound of example 4a therefore led to an increase in insulin sensitivity.

Figure 9:
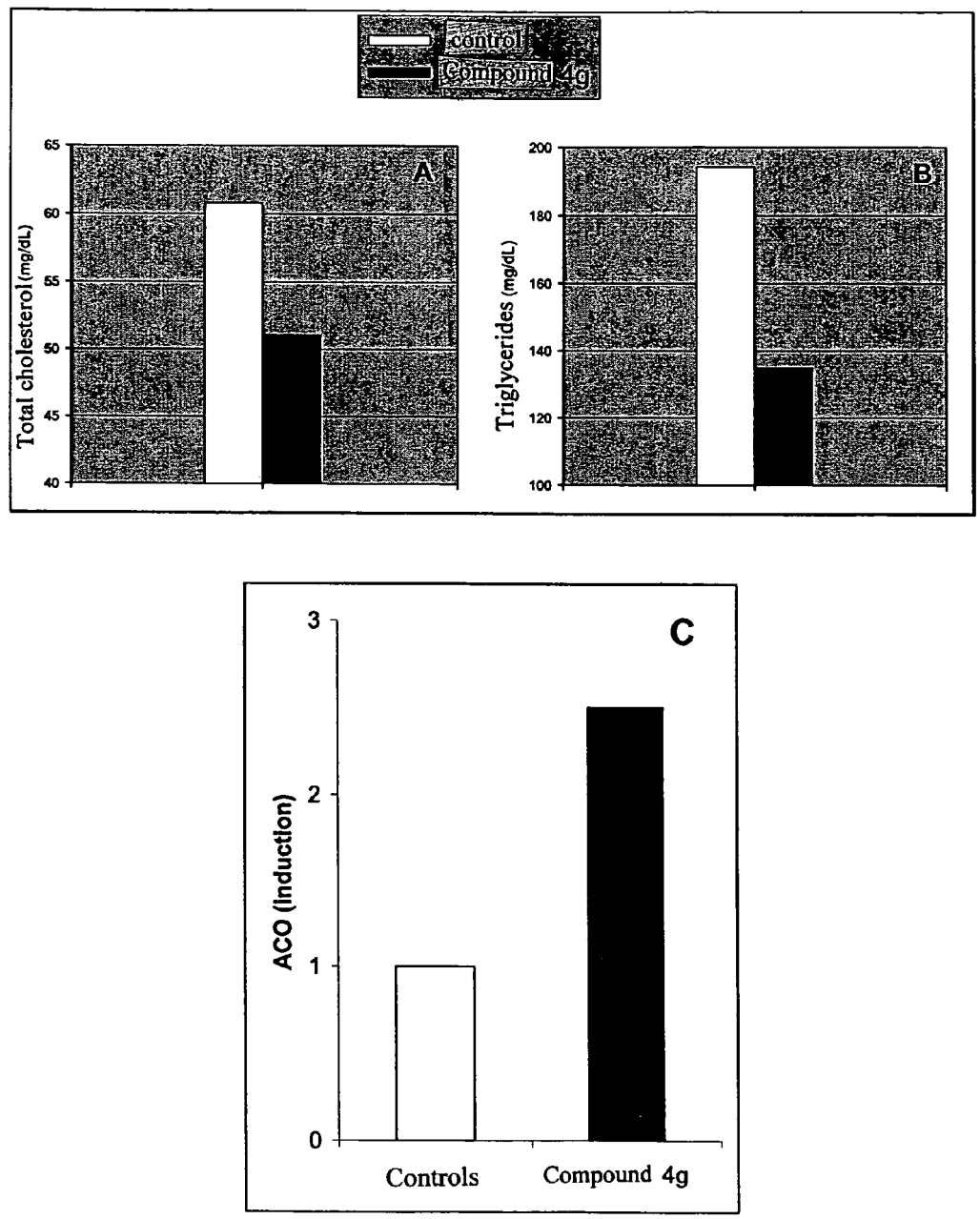

FIG. 9: Evaluation of the effects of compound 4g on plasma lipids and expression of a hepatic gene in rats.

FIGS. 9A and 9B show the effects of treating Wistar rats with the compound of example 4g (300 mg/kg/d) on plasma cholesterol and plasma triglycerides, respectively, after 14 days of treatment. The results show that treatment led to a decrease in circulating cholesterol and triglyceride levels. FIG. 9C shows the effects of treating Wistar rats with the compound of example 4g (300 mg/kg/d) on hepatic expression of a gene involved in peroxisomal β-oxidation of fatty acids (ACO). A marked activation of hepatic expression of the ACO gene, one of the main targets of PPARα, was observed.

Figure 10:
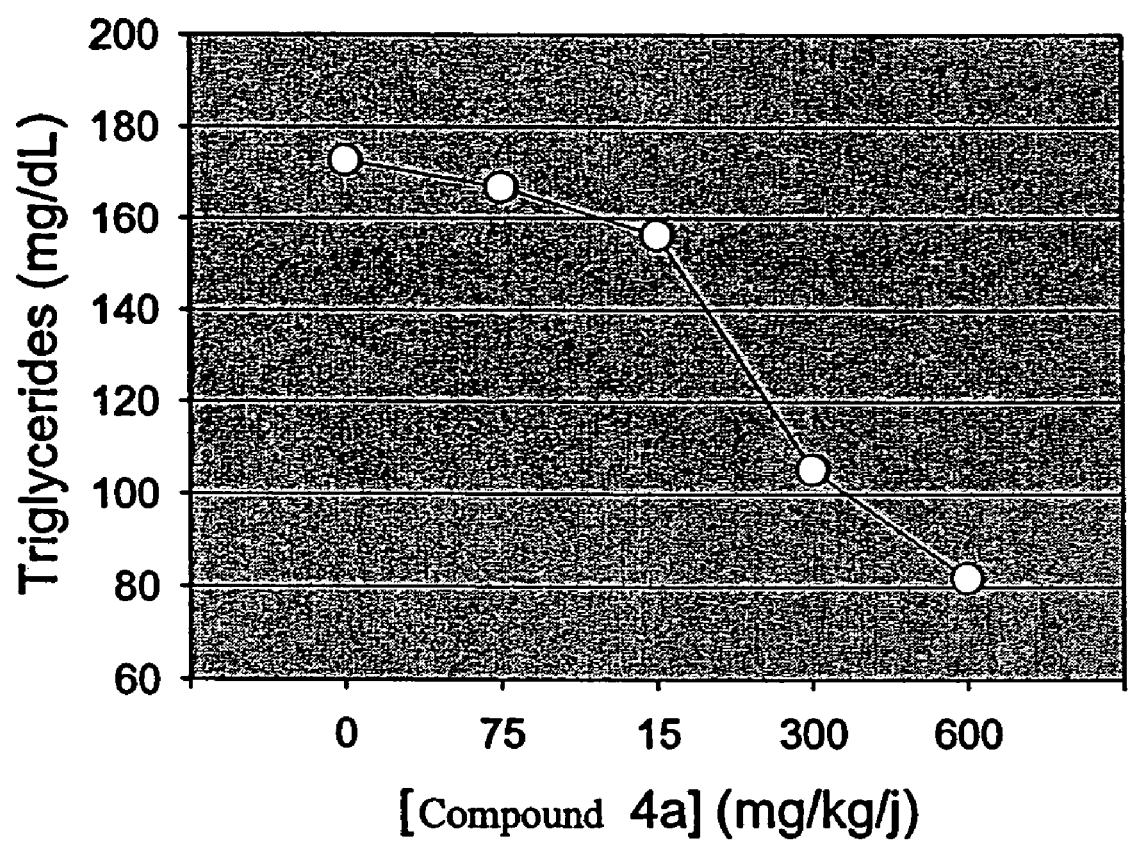

FIG. 10: Evaluation of the dose-effect relation for compound 4a on plasma triglyceride metabolism in Zucker rats.

FIG. 10 shows the effects of treating Zucker rats with the compound of example 4a at doses of 0 to 600 mg/kg/d on plasma triglyceride levels. A gradual dose-dependent decrease in triglyceride levels was seen.

Figure 11:
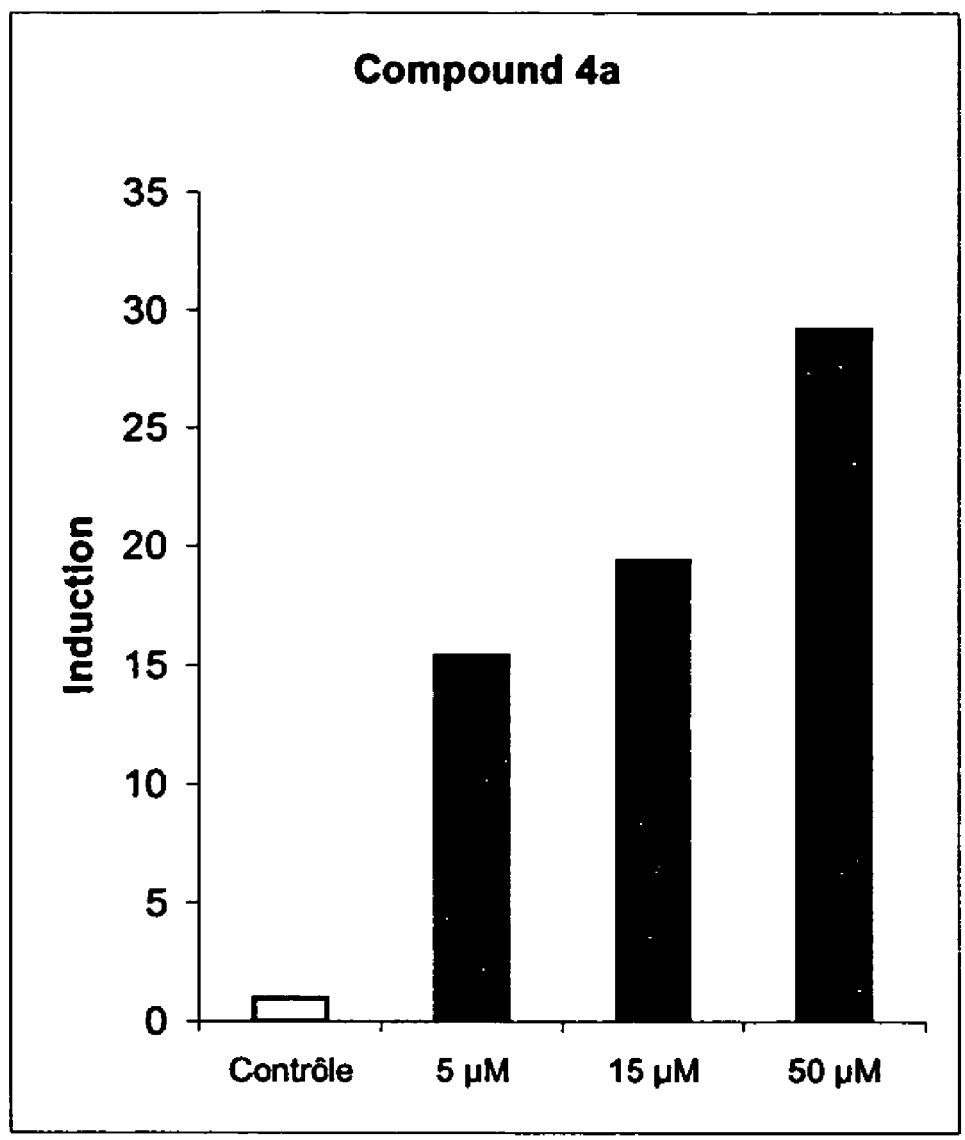

FIG. 11: Evaluation of the effects of compound 4a on PPARα activation in vitro.

FIG. 11 shows the effects of compound 4a on PPARα activation in vitro in HepG2 cells, evaluated by using a chimera composed of the DNA binding domain of the Gal4 transcription factor and the ligand binding domain of PPARα. The results show that the compound of example 4a induced a very strong activation of the PPARα nuclear receptor, and this in a dose-dependent manner.

Figure 12:
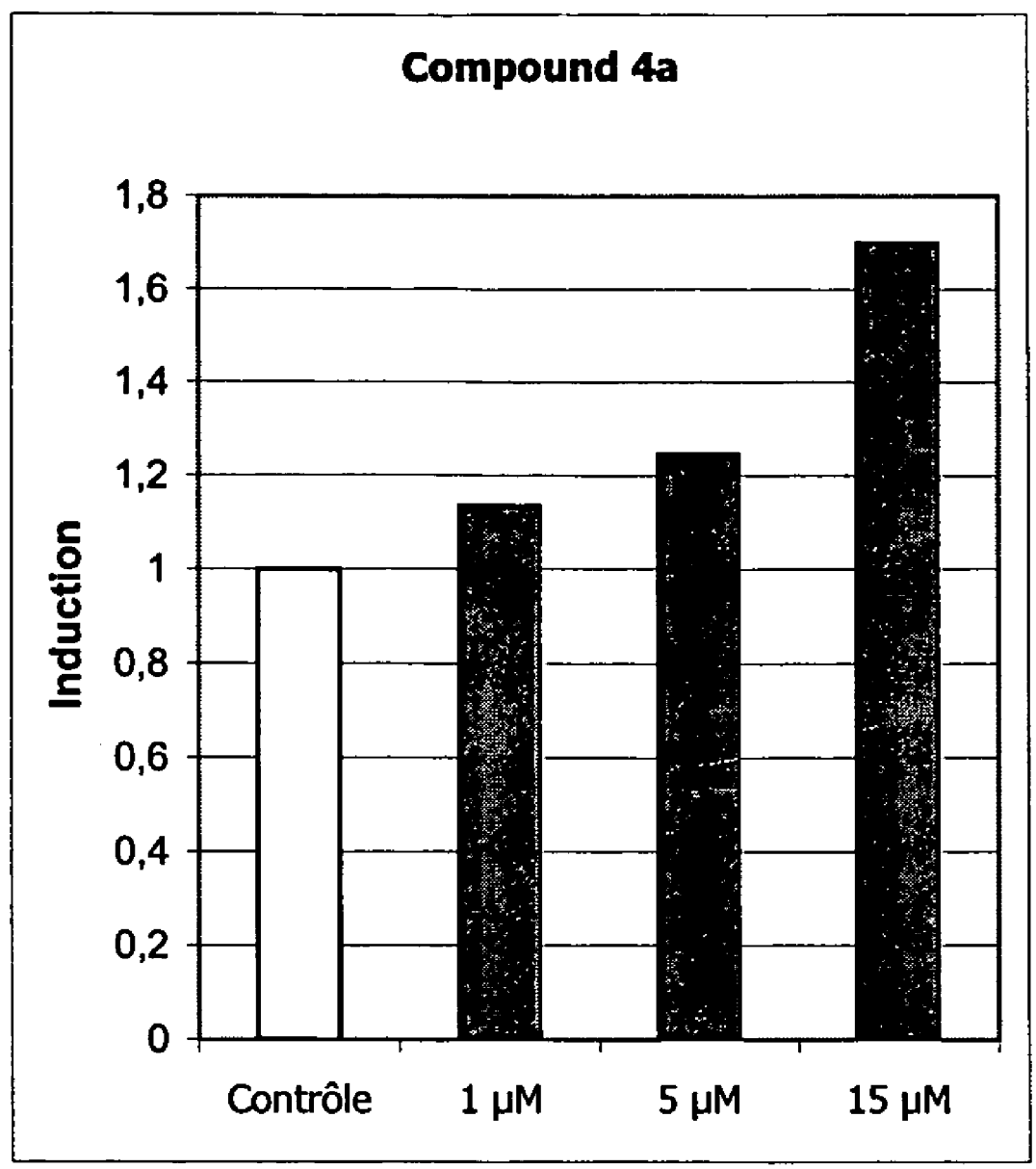

FIG. 12: Evaluation of the effects of compound 4a on ABCA1 gene expression in vitro in human macrophages.

FIG. 12 shows the effects of the compound of example 4a solubilized according to example 6, on ABCA-1 gene expression in vitro in human macrophages prepared as in example 12. The results show that the compound of example

EXAMPLES

Example 1

Preparation of Fatty Acid Derivatives

Example 1a

Preparation of Tetradecylthioacetic Acid

Potassium hydroxide (34.30 g, 0.611 mol), mercaptoacetic acid (20.9 ml, 0.294 mol) and 1-bromotetradecane (50 ml, 0.184 mol) were added in that order to methanol (400 ml). Said mixture was stirred overnight at room temperature. A concentrated hydrochloric acid solution (60 ml) dissolved in water (800 ml) was then added to the reaction mixture. Precipitation of tetradecylthioacetic acid occurred. The mixture was stirred overnight at room temperature. The precipitate was then filtered, washed five times with water and dried in a dessicator. The product was recrystallized in methanol (yield: 94%).

Rf ($CH_2Cl_2$—MeOH 9:1): 0.60.
MP°: 67-68° C.
IR: $\nu$CO acid 1726 and 1684 $cm^{-1}$.
NMR ($^1$H, $CDCl_3$): 0.84-0.95 (t, 3H, —$CH_3$, J=6.5 Hz); 1.20-1.45 (multiplet, 22H, —$CH_2$—); 1.55-1.69 (quint, 2H, —$CH_2$—$CH_2$—S—, J=6.5 Hz); 2.63-2.72 (t, 2H, $CH_2$—$CH_2$—S—, J=7.3 Hz); 3.27 (s, 2H, S—$CH_2$—COOH).
MS: M−1=287.

Example 1b

Preparation of 4-(dodecylthio)butanoic Acid

Dodecanethiol (2.01 g, 10 mmol) and ethyl bromobutyrate (1.971 g, 10 mmol) were stirred at room temperature under an inert atmosphere. Potassium hydroxide (1.36 g, 21 mmol) dissolved in 50 ml of ethanol was added slowly. The reaction mixture was heated under reflux for 3 hours. Ethanol was evaporated under vacuum. The residue was taken up in water and acidified. The precipitate which formed was filtered, washed with water and dried (yield 90%).

Rf ($CH_2Cl_2$-MeOH 9:1): 0.46.
IR: $\nu$CO acid 1689 $cm^{-1}$.
NMR ($^1$H, $CDCl_3$): 0.86-0.91 (t, 3H, —$CH_3$, J=6.2 Hz); 1.25-1.45 (multiplet, 18H, —$CH_2$); 1.53-1.63 (quint, 2H, —$CH_2$—$CH_2$—S—, J=6.7 Hz); 1.87-2.00 (quint, 2H, —$CH_2$—S—$CH_2$—$CH_2$—$CH_2$—COOH, J=7.2 Hz); 2.47-2.55 (m, 4H, —$CH_2$—S—$CH_2$—$CH_2$—$CH_2$—COOH); 2.55-2.62 (t, 2H, —$CH_2$—S—$CH_2$—$CH_2$—$CH_2$—COOH).
MS: M−1=287.

Example 1c

Preparation of 6-(decylthio)hexanoic Acid

Decanethiol (4.57 g, 25 mmol) and 4-bromobutyric acid (5 g, 25 mmol) were stirred at room temperature under an inert atmosphere. Potassium hydroxide dissolved in 50 ml of ethanol was added slowly. The reaction mixture was heated under reflux for 3 hours. Ethanol was evaporated under vacuum. The residue was taken up in water and acidified. The precipitate which formed was filtered, washed with water and dried (yield: 95%).

Rf ($CH_2Cl_2$-MeOH 9:1): 0.37.
IR: $\nu$CO acid 1690 $cm^{-1}$.
NMR ($^1$H, $CDCl_3$): 0.86-0.91 (t, 3H, —$CH_3$, J=6.5 Hz); 1.22-1.41 (multiplet, 14H, —$CH_2$—); 1.42-1.50 (m, 2H, $CH_2$—S—$CH_2$—$CH_2$—$CH_2$—$CH_2$—$CH_2$—COOH); 1.53-1.75 (multiplet, 6H, —$CH_2$—$CH_2$—S—$CH_2$—$CH_2$—$CH_2$—$CH_2$—$CH_2$—COOH); 2.35-2.42 (t, 2H, —$CH_2$—S—$CH_2$—$CH_2$—$CH_2$—$CH_2$—$CH_2$—COOH); 2.48-2.55 (multiplet, 4H, —$CH_2$—S—$CH_2$—).
MS: M−1=287.

Example 1d

Preparation of Tetradecylselenoacetic Acid

Preparation of Tetradecyldiselenide

Selenium (1.19 g, 15 mmol) was added under an inert atmosphere to a 1:1 mixture of THF/water (50 ml). After cooling the reaction mix in an ice bath, sodium tetraborohydride (1.325 g, 35 mmol) was slowly added. A second fraction of selenium (1.19, 15 mmol) was added. The reaction mixture was stirred at room temperature for 15 minutes then heated under reflux to dissolve all the reagents. Bromotetradecane (9 ml, 30 mmol) dissolved in 25 ml of THF was added. The reaction mixture was stirred at room temperature for 3 hours. The reaction mixture was then extracted with dichloromethane. The organic phases were combined, dried on magnesium sulfate, filtered and evaporated to dryness. The product was used without further purification.

Rf (petroleum ether): 0.77.
MP°: 43° C. (yellow crystals).
IR: $\nu$CH 2960-2850 $cm^{-1}$.
NMR ($^1$H, $CDCl_3$): 0.87-0.93 (t, 6H, —$CH_3$, J=6.5 Hz); 1.20-1.48 (multiplet, 40H, —$CH_2$—); 1.62-1.80 (m, 4H, —$CH_2CH_2$—Se—); 2.88-2.96 (t, 4H, —$CH_2$—$CH_2$—Se—).

Preparation of Tetradecylselenoacetic Acid

In an inert atmosphere, ditetradecyldiselenide (8.5 g, 17 mmol) was dissolved in a mixture of THF/water (150 ml/50 ml) and cooled in an ice bath. Sodium tetraborohydride (2.9 g, 61 mmol) was added slowly (the solution blanches) followed by bromoacetic acid (8.5 g, 61 mmol) dissolved in a mixture of THF/water (25 ml/25 ml). The reaction mixture was stirred at room temperature for 6 hours. The reaction mixture was then extracted with ether and the aqueous phase was acidified. The resulting precipitate was filtered, washed several times with water and dried (yield: 29%).

Rf ($CH_2Cl_2$-MeOH 9:1): 0.60.
MP°: 68° C.
IR: $\nu$CO acid 1719 and 1680 $cm^{-1}$.
NMR ($^1$H, $CDCl_3$): 0.85-0.95 (t, 3H, —$CH_3$, J=6.5 Hz); 1.25-1.48 (multiplet, 22H, —$CH_2$—); 1.65-1.78 (quint, 2H, —$CH_2$—$CH_2$—Se—, J=6.5 Hz); 2.78-2.84 (t, 2H, $CH_2$—$CH_2$—Se—, J=7 Hz); 3.18 (s, 2H, Se—$CH_2$—COOH).
MS: M−1=335.

Example 1e

Preparation of Tetradecylsulfoxyacetic Acid

Tetradecylthioacetic acid (5 g, 17.4 mmol) (example 1a) was dissolved in a mixture of methanol/dichloromethane (160 ml/80 ml). The reaction mixture was stirred and cooled in an ice bath before slowly adding Oxone® (12.8 g, 21 mmol) dissolved in water (160 ml). The reaction mixture was stirred at room temperature for 3 hours. The solvents were evaporated under vacuum. The precipitate which formed in the remaining aqueous phase was drained, washed several times with water and dried (yield: 90%).

Rf (CH$_2$Cl$_2$-MeOH 9:1): 0.27.

IR: νCO acid 1723 and 1690 cm$^{-1}$.

NMR ($^1$H, DMSO): 0.80-0.92 (t, 3H, —CH$_3$, J=6.4 Hz); 1.19-1.50 (multiplet, 22H, —CH$_2$—); 1.55-1.71 (quint, 2H, —CH$_2$—CH$_2$—SO—); 2.70-2.89 (t, 2H, —CH$_2$—CH$_2$—SO—CH$_2$—COOH, J=6.7 Hz); 3.52-3.70 (d, 1H, —CH$_2$—SO—CH$_2$—COOH, J=14.5 Hz); 3.80-3.95 (d, 1H, —CH$_2$—SO—CH$_2$—COOH, J=14.1 Hz).

MS: M+1=305; M+23=327 (M+Na$^+$); M+39=343 (M+K$^+$).

Example 1f

Preparation of 6-(decylsulfoxy)hexanoic Acid

The product was prepared according to the procedure described hereinabove (example 1e) from 6-(decylthio)hexanoic acid (example 1c).

Yield: 94%.

Rf (CH$_2$Cl$_2$-MeOH 9:1): 0.18.

NMR ($^1$H, CDCl$_3$): 0.86-0.91 (t, 3H, —CH$_3$, J=6.8 Hz); 1.20-1.40 (multiplet, 14H, —CH$_2$—); 1.40-1.60 (m, 2H, CH$_2$—SO—CH$_2$—CH$_2$—CH$_2$—CH$_2$—CH$_2$—COOH); 1.63-1.95 (multiplet, 6H, —CH$_2$—CH$_2$—S—CH$_2$—CH$_2$—CH$_2$—CH$_2$—CH$_2$—COOH); 2.35-2.42 (m, 3H, —CH$_2$—S—CH$_2$—CH$_2$—CH$_2$—CH$_2$—CH$_2$—COOH and —CH$_2$—SO—CH$_2$—CH$_2$—CH$_2$—CH$_2$—CH$_2$—COOH); 2.60-2.71 (m, 1H, —CH$_2$—SO—CH$_2$—CH$_2$—CH$_2$—CH$_2$—CH$_2$—COOH); 2.75-2.85 (m, 1H, —CH$_2$—SO—(CH$_2$)$_5$—COOH); 2.80-3.01 (m, 1H, —CH$_2$—SO—(CH$_2$)$_5$—COOH).

Example 1g

Preparation of Tetradecylsulfonylacetic Acid

Tetradecylthioacetic acid (5 g, 17.4 mmol) (example 1a) was dissolved in a mixture of methanol/dichloromethane (160 ml/80 ml). The reaction mixture was stirred and cooled in an ice bath before slowly adding Oxone® (21.8 g, 35 mmol) dissolved in water (160 ml). The reaction mixture was stirred at room temperature for 3 hours. The solvents were evaporated under vacuum. The precipitate which formed in the remaining aqueous phase was drained, washed several times with water and dried (yield: 89%).

Rf (CH$_2$Cl$_2$-MeOH 9:1): 0.21.

IR: νCO acid 1701 cm$^{-1}$.

NMR ($^1$H, DMSO): 0.85-0.96 (t, 3H, —CH$_3$, J=6 Hz); 1.20-1.40 (multiplet, 22H, —CH$_2$—); 1.40-1.55 (m, 2H, —CH$_2$—CH$_2$—CH$_2$—SO$_2$—); 1.80-1.96 (m, 2H, —CH$_2$—CH$_2$—SO$_2$—); 3.22-3.34 (t, 2H, —CH$_2$—CH$_2$—SO$_2$—CH$_2$—COOH, J=8 Hz); 4.01 (s, 2H, —CH$_2$—SO$_2$—CH$_2$—COOH).

MS: M−1=319.

Example 1h

Preparation of 6-(decylsulfonyl)hexanoic Acid

The product was prepared according to the procedure described hereinabove (example 1g) from 6-(decylthio)hexanoic acid (example 1c).

Yield: 87%.

Rf (CH$_2$Cl$_2$-MeOH 9:1): 0.15.

IR: νCO acid 1689 cm$^{-1}$.

NMR ($^1$H, CDCl$_3$): 0.85-0.96 (t, 3H, —CH$_3$, J=6.5 Hz); 1.22-1.40 (multiplet, 12H, —CH$_2$—); 1.40-1.61 (multiplet, 4H, —SO$_2$—CH$_2$—CH$_2$—CH$_2$—); 1.65-1.95 (multiplet, 6H, —CH$_2$—CH$_2$—SO$_2$—CH$_2$—CH$_2$—CH$_2$—CH$_2$—CH$_2$—COOH); 2.35-2.46 (m, 2H, —CH$_2$—COOH); 2.60-2.84 (m, 2H, —CH$_2$—SO$_2$—CH$_2$—CH$_2$—CH$_2$—CH$_2$—CH$_2$—COOH); 2.90-3.02 (m, 2H, —CH$_2$—SO$_2$—CH$_2$—CH$_2$—CH$_2$—CH$_2$—COOH).

Example 1i

Preparation of Docosylthioacetic Acid

The product was obtained according to the procedure described hereinabove (example 1a) from mercaptoacetic acid and bromodocosane.

Yield: 90%.

Rf (CH$_2$Cl$_2$-MeOH 9:1): 0.62.

IR: νCO acid 1728 and 1685 cm$^{-1}$.

NMR ($^1$H, CDCl$_3$): 0.83-0.94 (t, 3H, —CH$_3$, J=6.6 Hz); 1.18-1.48 (multiplet, 38H, —CH$_2$—); 1.55-1.69 (quint, 2H, —CH$_2$—CH$_2$—S—, J=6.7 Hz); 2.63-2.72 (t, 2H, CH$_2$—CH$_2$—S—, J=7.3 Hz); 3.26 (s, 2H, S—CH$_2$—COOH).

Example 2

Preparation of Monoacylglycerols

Example 2a

Preparation of 1-tetradecylthioacetylglycerol

Preparation of (2,3-O-isopropylidene)propyl Tetradecylthioacetate

In a flask immersed in an ice bath, tetradecylthioacetic acid (4 g, 13.86 mmol) was dissolved in tetrahydrofuran (100 ml) after which EDCl (2.658 g, 13.86 mmol), dimethylaminopyridine (1.694 g, 13.86 mmol) and solketal (1.72 ml, 13.86 mmol) were added in that order. The reaction mixture was stirred at room temperature for 4 days. The solvent was evaporated under vacuum. The residue was taken up in dichloromethane, washed with an aqueous solution of 1 N HCl then with an aqueous solution of 10% NaHCO$_3$ and lastly with a saturated NaCl solution. The organic phase was dried on magnesium sulfate, filtered and evaporated under vacuum. The residual oil was purified by silica gel chromatography (ethyl acetate-cyclohexane 1:9). The product was obtained as a yellow oil (yield: 80%).

Rf (cyclohexane-ethyl acetate 8:2): 0.65.

IR: νCOester 1736 cm$^{-1}$.

NMR ($^1$H, CDCl$_3$): 0.86 (t, 3H, —CH$_3$, J=7.8 Hz); 1.25 (multiplet, 20H, —CH$_2$—); 1.33 (s, 3H, CH$_3$ isopropylidene); 1.37 (s, 3H, CH$_3$ isopropylidene); 1.59 (m, 4H, OCO—CH$_2$—CH$_2$—CH$_2$—); 2.62 (t, 2H, —O—CO—CH$_2$—S—CH$_2$—, J=7.40 Hz); 3.25 (s, 2H, —O—CO—CH$_2$—S—CH$_2$—); 3.75 (m, 1H, —CO—O—CH$_2$—CH (isopropylidene)); 4.08 (m, 2H, —CO—O—CH$_2$—CHCH$_2$ (isopropylidene)); 4.18 (m, 1H, —CO—O—CH$_2$-isopropylidene); 4.35 (m, 1H, —CO—O—CH$_2$-isopropylidene).

Preparation of 1-tetradecylthioacetylglycerol (2,3-O-isopropylidene)propyl tetradecylthioacetate (4.163 g, 10.356 mmol) was dissolved in acetic acid (60 ml) and stirred at room temperature. After 11 days of reaction, the reaction mixture was diluted in water, then extracted with ethyl acetate. The organic phase was washed with a saturated aqueous NaCl solution then dried on magnesium sulfate, filtered and the solvent was evaporated. The resulting white powder was recrystallized in heptane (yield: 90%).

Rf (ethyl acetate-cyclohexane 5:5): 0.30.
MP°: 63-65° C.
IR: νCO ester 1720 $cm^{-1}$.
NMR ($^1$H, CDCl$_3$): 0.89 (t, 3H, —CH$_3$, J=6.6 Hz); 1.28 (multiplet, 20H, —CH$_2$—); 1.59 (multiplet, 4H, —CH$_2$—CH$_2$—CH$_2$—S—); 2.64 (t, 2, CH$_2$—CH$_2$—S—, J=7.23 Hz); 3.26 (s, 2H, S—CH$_2$—COOH); 3.64 (m, 2H, —COO—CH$_2$—CHOH—CH$_2$OH); 3.97 (m, 1H, —COO—CH$_2$—CHOH—CH$_2$OH); 4.27 (m, 2H, —COO—CH$_2$—CHOH—CH$_2$OH).
MS: M+23=385 (M+Na$^+$) (M+H not detected).

Example 2b

Preparation of 1-palmitoylglycerol

This compound was synthesized according to the procedure described hereinabove (example 2a) starting from solketal and palmitic acid.

(2,3-O-isopropylidene)propyl Palmitate
Yield: 55%.
Rf (CH$_2$Cl$_2$): 0.35.
MP°: 32-33° C.
IR: νCOester 1733 $cm^{-1}$.
NMR ($^1$H, CDCl$_3$): 0.89 (t, 3H, —CH$_3$, J=6.6 Hz); 1.27 (multiplet, 24H, —CH$_2$—); 1.39 (s, 3H, CH$_3$ isopropylidene); 1.45 (s, 3H, CH$_3$ isopropylidene); 1.62 (m, 4H, OCO—CH$_2$—CH$_2$—CH$_2$—); 2.32 (t, 2H, —O—CO—CH$_2$—CH$_2$—CH$_2$—, J=7.40 Hz); 3.75 (dd, 1H, —CO—O—CH$_2$—CH(isopropylidene), J=8.3 Hz and J=2.1 Hz); 4.10 (m, 2H, —CO—O—CH$_2$—CHCH$_2$(isopropylidene)); 4.18 (dd, 1H, —CO—O—CH$_2$-isopropylidene, J=11.6 Hz and J=4.6 Hz); 4.33 (m, 1H, —CO—O—CH$_2$-isopropylidene).

1-palmitoylglycerol
Yield: 84%.
Rf (ethyl acetate-cyclohexane 5:5): 0.30.
MP°: 72-74° C.
IR: νCO ester 1730 $cm^{-1}$.
NMR ($^1$H, CDCl$_3$): 0.89 (t, 3H, —CH$_3$, J=6.5 Hz); 1.26 (multiplet, 24H, —CH$_2$—); 1.64 (m, 2H, OCO—CH$_2$—CH$_2$—CH$_2$—); 2.36 (t, 2H, —O—CO—CH$_2$—CH$_2$—CH$_2$—, J=7.40 Hz); 3.60 (dd, 1H, —CO—O—CH$_2$—CHOH—CH$_2$OH, J=11.8 Hz and J=6.1 Hz); 3.71 (dd, 1H, —CO—O—CH$_2$—CHOH—CH$_2$OH, J=11.8 Hz and J=3.9 Hz); 3.94 (m, 1H, —CO—O—CH$_2$—CHOH—CH$_2$OH); 4.19 (m, 2H, —CO—O—CH$_2$—CHOH—CH$_2$OH).

Example 2c

Preparation of 2-tetradecylthioacetylglycerol

Preparation of 1,3-benzylideneglycerol
Glycerol (30 g, 0.326 mol), benzaldehyde (34.5 g, 0.326 mol) and p-toluene sulfonic acid (50 mg) were dissolved in 350 ml of toluene and placed under reflux in a Dean-Stark apparatus for 18 hours. The reaction mixture was dried. The residual product was purified by silica gel chromatography (eluent:cyclohexane/ethyl acetate 8:2 then 7:3) and recrystallized (yield: 20%).
Rf (ethyl acetate-cyclohexane 5:5): 0.34.
IR: νOH 3286 $cm^{-1}$.
NMR ($^1$H, CDCl$_3$): 3.19 (sl, 1H exchangeable, —OH); 3.64 (sl, 1H, —O—CH$_2$—CHOH—CH$_2$O—); 3.99-4.16 (dd, 2H, —O—CHaHb—CHOH—CHaHbO—, J=1.1 Hz and J=10.4 Hz); 4.17-4.23 (dd, 2H, —O—CHaHb—CHOH—CHaHbO—, J=1.6 Hz and J=11.5 Hz); 5.57 (s, 1H, Φ—CH—); 7.34-7.45 (m, 3H, H aromatic); 7.49-7.55 (m, 2H, H aromatic).

Preparation of (1,3-O-benzylidene)propyl Tetradecylthioacetate
In a flask immersed in an ice bath, tetradecylthioacetic acid (0.800 g, 2.774 mmol) was dissolved in THF (75 ml) followed by addition of EDCl (0.532 g, 2.774 mmol), dimethylaminopyridine (0.339 g, 2.774 mmol) and 1,3-benzylideneglycerol (0.5 g, 2.774 mmol) in that order. The mixture was stirred at room temperature for 16 hours. The solvent was evaporated. The residue was taken up in dichloromethane, washed with 1 N hydrochloric acid then with a 10% potassium carbonate solution and lastly with a saturated aqueous NaCl solution. The organic phase was dried on MgSO$_4$, filtered and dried. The residue was taken up in petroleum ether. The precipitate which formed was filtered, then purified by silica gel chromatography (eluent:ethyl acetate-cyclohexane 2:8) to produce the desired compound as a white powder (yield : 50%).
Rf (ethyl acetate-cyclohexane 2:8): 0.53.
MP°: 51-53° C.
IR: νCO ester 1723 $cm^{-1}$.
NMR ($^1$H, CDCl$_3$): 0.85-0.96 (t, 3H, CH$_3$, J=6.8 Hz); 1.19-1.44 (multiplet, 20H, —CH$_2$); 1.52-1.69 (multiplet, 4H, —CH$_2$—CH$_2$—CH$_2$—S—); 2.62-2.80 (t, 2H, —CH$_2$—CH$_2$—CH$_2$—S—, J=7.2 Hz); 3.34 (s, 2H, —CH$_2$—S—CH$_2$—COO—); 4.12-4.29 (dd, 2H, —O—CHaHb—CHOH—CHaHbO—, J=1.7 Hz and J=13.1 Hz); 4.30-4.41 (dd, 2H, —O—CHaHb—CHOH—CHaHbO—, J=1.3 Hz and J=13.1 Hz); 4.75-4.79 (t, 1H, —O—CH$_2$—CHOH—CH$_2$O—, J=1.7 Hz); 5.59 (s, 1H, Φ—CH—); 7.35-7.45 (m, 3H, H aromatic); 7.48-7.57 (m, 2H, H aromatic).

Preparation du 2-tetradecylthioacetylglycerol
(1,3-O-benzylidene)propyl tetradecylthioacetate (0.576 g, 1.278 mmol) was dissolved in a 50:50 (v/v) mixture of dioxane and triethylborate followed by addition of boric acid (0.317 g, 5.112 mmol). The reaction mixture was heated at 100° C. for 4 hours. Two equivalents of boric acid (0.158 g, 2.556 mmol) were added followed by 2 equivalents after 5.5 hours and 7 hours of reaction. After 24 hours of reaction, the triethylborate was evaporated. The residue was taken up in ethyl acetate and washed with water. The aqueous phase was neutralized with NaHCO$_3$ then extracted with dichloromethane. The organic phase was washed with a saturated aqueous NaCl solution, dried on MgSO$_4$, filtered and dried. The residue was purified by silica gel chromatography (eluent:ethyl acetate-cyclohexane 5:5) (yield : 62%).
Rf (ethyl acetate-cyclohexane 7-3): 0.51.
IR: νCO ester 1739 $cm^{-1}$.
NMR ($^1$H, CDCl$_3$): 0.82-0.95 (t, 3H, —CH$_3$, J=6.9 Hz); 1.15-1.35 (multiplet, 22H, —CH$_2$—); 1.55-1.68 (m, 2H, —CH$_2$—CH$_2$—S—); 2.23 (sl, 2H, OH); 2.65 (m, 2H, CH$_2$—CH$_2$—S—); 3.26 (s, 2H, S—CH$_2$—COOH); 3.64-3.73 (m, 4H, —COO—CH$_2$—CHOH—CH$_2$OH); 3.97 (m,1H, —COO—CH$_2$—CHOH—CH$_2$OH).

Example 3

Preparation of 1,3-diacylglycerols

Example 3a

Preparation of 1,3-dipalmitoylglycerol

Glycerol (10 g, 0.109 mol, 1 eq), palmitic acid (55.69 g, 0.217 mol, 2 eq), dicyclohexylcarbodiimide (44.77 g, 0.217 mol, 2 eq) and dimethylaminopyridine (26.51 g, 0.217 mol, 2 eq) were dissolved in dichloromethane. The reaction mixture was stirred at room temperature for 48 hours. The dicyclohexylurea formed was filtered and washed several times with dichloromethane. The filtrate was dried. The residual product was purified by silica gel chromatography (eluent:dichloromethane) (yield: 45%).

Rf ($CH_2Cl_2$): 0.30.
MP°: 70-73° C.
IR: νCO ester 1735 and 1716 $cm^{-1}$.
NMR ($^1H$, $CDCl_3$): 0.86-91 (t, 6H, —$CH_3$, J=6.5 Hz); 1.27 (multiplet, 48H, —$CH_2$—); 1.60-1.65 (quint, 4H, $OCOCH_2$—$CH_2$—, J=7.4 Hz); 2.32-2.38 (t, 4H, $OCOCH_2$—$CH_2$—, J=7.6 Hz); 2.51-2.52 (d, 1H, OH (exchangeable)); 4.06-4.21 (multiplet, 5H, —$CH_2$—CH—$CH_2$—).
MS: M+23=591 (M+$Na^+$); M+39=607 (M+$K^+$); (M+H not detected).

Example 3b

Preparation of 1,3-dilinoleylglycerol

This compound was obtained according to the procedure described hereinabove (example 3a) from glycerol and linoleic acid. The product was obtained as a colorless oil (yield : 26%).

Rf ($CH_2Cl_2$): 0.30.
IR: νCO ester 1743 and 1719 $cm^{-1}$.
NMR ($^1H$, $CDCl_3$): 0.83-0.93 (t, 6H, —$CH_3$, J=6.5 Hz); 1.15-1.44 (multiplet, 28H, —$CH_2$—); 1.55-1.70 (quint, 4H, $OCOCH_2$—$CH_2$—, J=7.4 Hz); 1.90-2.15 (multiplet, 8H, —$CH_2$—CH═CH—$CH_2$—CH═CH—$CH_2$—); 2.30-2.41 (t, 4H, $OCOCH_2$—$CH_2$—, J=7.6 Hz); 2.48-2.52 (d, 1H, OH (exchangeable)); 2.70-2.83 (t, 4H, —$CH_2$—CH═CH—$CH_2$—CH═CH—$CH_2$—); 4.05-4.25 (multiplet, 5H, —CHaHb—CH—CHaHb-); 5.25-5.46 (m, 8H, —$CH_2$—CH═CH—$CH_2$—CH═CH—$CH_2$—).
MS: M+23=639 (M+$Na^+$); M+39=655 (M+$K^+$); (M+H not detected).

Example 3c

Preparation of 1,3-distearylglycerol

This compound was obtained according to the procedure described hereinabove (example 3a) from glycerol and stearic acid. The product was obtained as a white powder (yield: 21%).

Rf ($CH_2Cl_2$): 0.30.
IR: νCO ester 1735 and 1716 $cm^{-1}$.
NMR ($^1H$, $CDCl_3$): 0.83-0.91 (t, 6H, —$CH_3$, J=6.5 Hz); 1.27 (multiplet, 56H, —$CH_2$—); 1.59-1.66 (quint, 4H, $OCOCH_2$—$CH_2$—, J=7.4 Hz); 2.33-2.38 (t, 4H, $OCOCH_2$—$CH_2$—, J=7.5 Hz); 2.45-2.47 (d, 1H, OH (exchangeable), J=4.3 Hz); 4.08-4.23 (multiplet, 5H, —CHaHb—CH—CHaHb—).
MS: M+23=647 (M+$Na^+$); (M+H not detected).

Example 3d

Preparation of 1,3-dioleylglycerol

This compound was obtained according to the procedure described hereinabove (example 3a) from glycerol and oleic acid. The product was obtained as a colorless oil (yield: 15%).

Rf ($CH_2Cl_2$): 0.23.
IR: νCO ester 1743 and 1720 $cm^{-1}$.
NMR ($^1H$, $CDCl_3$): 0.89 (t, 6H, —$CH_3$, J=7.2 Hz); 1.30 (multiplet, 40H, —$CH_2$—); 1.64 (quint, 4H, $OCOCH_2$—$CH_2$—, J=7.4 Hz); 2.02 (multiplet, 8H, —$CH_2$—CH═CH—$CH_2$—); 2.36 (t, 4H, $OCOCH_2$—$CH_2$—, J=7.2 Hz); 2.45 (d, 1H, OH (exchangeable), J=4.2 Hz); 4.18 (multiplet, 5H, —CHaHb—CH—CHaHb—); 5.35 (m, 4H, —$CH_2$—CH═CH—$CH_2$—).
MS: M+23=643 (M+$Na^+$); (M+H not detected).

Example 3e

Preparation of 1,3-ditetradecanoylglycerol

This compound was obtained according to the procedure described hereinabove (example 3a) from glycerol and tetradecanoic acid. The product was obtained as a white powder (yield: 30%).

Rf ($CH_2Cl_2$): 0.30.
IR: νCO ester 1733 and 1707 $cm^{-1}$.
NMR ($^1H$, $CDCl_3$): 089 (t, 6H, —$CH_3$, J=6.5 Hz); 1.26 (multiplet, 40H, —$CH_2$—); 1.62 (quint, 4H, $OCOCH_2$—$CH_2$—, J=7.4 Hz); 2.36 (t, 4H, $OCOCH_2$—$CH_2$—, J=7.5 Hz); 2.45 (d, 1H, OH (exchangeable), J=4.3 Hz); 4.15 (multiplet, 5H, —CHaHb—CH—CHaHb—).

Example 3f

Preparation of 1-oleyl-3-palmitoylglycerol

Glycerol palmitate (example 2b) (5.516 g, 0.017 mol) was dissolved in dichloromethane (500 ml) and dicyclohexylcarbodiimide (5.165 g, 0.025 mol), dimethylaminopyridine (3.058 g, 0.025 mol) and oleic acid (4.714 g, 0.017 mol) were then added. The reaction mixture was stirred at room temperature for 24 hours. The dicyclohexylurea precipitate was filtered, washed with dichloromethane and the filtrate was evaporated under vacuum. The residue obtained was purified by silica gel chromatography (eluent:$CH_2Cl_2$) to give the desired compound as a white solid (yield: 23%).

Rf ($CH_2Cl_2$): 0.24.
MP°: 30° C.
IR: νCO ester 1731 and 1710 $cm^{-1}$.
NMR ($^1H$, $CDCl_3$): 087 (t, 6H, —$CH_3$, J=6.5 Hz); 1.26 (multiplet, 44H, —$CH_2$—); 1.62 (quint, 4H, $OCOCH_2$—$CH_2$—, J=7.4 Hz); 2.01 (multiplet, 4H, —$CH_2$—CH═CH—$CH_2$—); 2.36 (t, 4H, $OCOCH_2$—$CH_2$—, J=7.3 Hz); 2.465 (d, 1H, OH (exchangeable), J=4.3 Hz); 4.17 (multiplet, 5H, —CHaHb—CH—CHaHb—); 5.34 (m, 4H, —$CH_2$—CH═CH—$CH_2$—).
MS: M+23=617 (M+$Na^+$); (M+H not detected).

Example 4

Preparation of 1,2,3-triacylglycerols

Example 4a

Preparation of 1,2,3-tritetradecylthioacetylglycerol

Glycerol (1 g, 10.86 mmol) was dissolved in dichloromethane (200 ml) and dicyclohexylcarbodiimide (7.84 g, 38.01 mmol), dimethylaminopyridine (4.64 g, 38.01 mmol) and tetradecylthioacetic acid (9.40 g, 32.58 mmol) were then added. The mixture was stirred at room temperature. After 48 hours of reaction, the dicyclohexylurea precipitate was filtered, washed with dichloromethane and the filtrate was evaporated. The residue obtained was purified by silica gel chromatography (eluent:$CH_2Cl_2$-cyclohexane 4-6). 1,2,3-tritetradecylthioacetylglycerol was obtained as a white powder (yield: 65%).

Rf ($CH_2Cl_2$-Cyclohexane 7:3): 0.47.
MP°: 57° C.
IR: νCO ester 1738 and 1722 $cm^{-1}$.
NMR ($^1H$, $CDCl_3$): 0.89 (t, 9H, —$CH_3$, J=6.5 Hz); 1.26 (multiplet, 66H, —$CH_2$—); 1.62 (m, 6H, —$CH_2$—$CH_2$—$CH_2$—S—); 2.63 (t, 6H, $CH_2$—$CH_2$—S—, J=7.3 Hz); 3.23 (s, 6H, S—$CH_2$—COOH); 4.27 (dd, 2H, —CHaHb—CH—CHaHb—, J=12 Hz and J=6 Hz); 4.39 (dd, 2H, —CHaHb—CH—CHaHb—, J=12 Hz and J=4.3 Hz); 5.34 (m, 1H, —CHaHb—CH—CHaHb—).
MS: M+23=925 (M+$Na^+$); M+39=941 (M+$K^+$); 903 (M+H not detected).

Example 4b

Preparation of 1,2,3-tri-(4-dodecylthio)butanoylglycerol

This compound was obtained according to the procedure described hereinabove (example 4a) from 4-(dodecylthio)butanoic acid (example 1b) and glycerol.

Rf ($CH_2Cl_2$-Cyclohexane 7:3): 0.43.
IR: νCO ester 1738 and 1727 $cm^{-1}$.
NMR ($^1H$, $CDCl_3$): 0.84-0.92 (t, 9H, —$CH_3$, J=6.3 Hz); 1.22-1.44 (multiplet, 54H, —$CH_2$—); 1.50-1.64 (multiplet, 6H, —$CH_2$—$CH_2$—S—$CH_2$—$CH_2$—$CH_2$—COOH); 1.83-1.97 (multiplet, 6H, —$CH_2$—S—$CH_2$—$CH_2$—$CH_2$—COOH); 2.42-2.59 (multiplet, 18H, —$CH_2$—$CH_2$—$CH_2$—S—$CH_2$—$CH_2$—$CH_2$—COOH); 4.11-4.20 (dd, 2H, —CHaHb—CH—CHaHb—, J=12 Hz and J=5.9 Hz); 4.29-4.36 (dd, 2H, —CHaHb—CH—CHaHb—, J=12 Hz and J=4.5 Hz); 5.22-5.32 (m, 1H, —CHaHb—CH—CHaHb—).
MS: M+23=925 (M+$Na^+$); M+39=941 (M+$K^+$); 903 (M+H not detected).

Example 4c

Preparation of 1,2,3-tri-(6-decylthio)hexanoylglycerol

This compound was obtained according to the procedure described hereinabove (example 4a) from 6-(decylthio)hexanoic acid (example 1c) and glycerol.

Rf ($CH_2Cl_2$-Cyclohexane 7:3): 0.43.
IR: νCO ester 1730 $cm^{-1}$.
NMR ($^1H$, $CDCl_3$): 0.85-0.92 (t, 9H, —$CH_3$, J=6.5 Hz); 1.21-1.50 (multiplet, 48H, —$CH_2$—); 1.51-1.72 (multiplet, 18H, —$CH_2$—$CH_2$—S—$CH_2$—$CH_2$—$CH_2$—$CH_2$—$CH_2$—COOH); 2.28-2.40 (multiplet, 6H, —$CH_2$—S—$CH_2$—$CH_2$—$CH_2$—$CH_2$—$CH_2$—COOH); 2.45-2.57 (multiplet, 12H, —$CH_2$—S—$CH_2$—); 4.10-4.20 (dd, 2H, —CHaHb—CH—CHaHb—, J=12 Hz and J=6 Hz); 4.25-4.38 (dd, 2H, —CHaHb—CH—CHaHb—, J=12 Hz and J=4.3 Hz); 5.22-5.32 (m, 1H, —CHaHb—CH—CHaHb—).
MS: M+23=925 (M+$Na^+$); M+39=941 (M+$K^+$); 903 (M+H not detected).

Example 4d

Preparation of 1,2,3-tritetradecylsulfoxyacetylglycerol

This compound was obtained according to the procedure described hereinabove (example 4a) from tetradecylsulfoxyacetic acid (example 1e) and glycerol.

Rf ($CH_2Cl_2$-Cyclohexane 7:3): 0.33.
IR: νCO ester 1730 $cm^{-1}$.
NMR ($^1H$, $CDCl_3$): 0.84-0.92 (t, 9H, —$CH_3$, J=6.7 Hz); 1.22-1.39 (multiplet, 66H, —$CH_2$—); 1.40-1.54 (multiplet, 6H, —$CH_2$—$CH_2$—SO—); 2.82-2.89 (multiplet, 6H, —$CH_2$—$CH_2$—SO—$CH_2$—COO—); 3.68 (s, 6H, —$CH_2$—SO—$CH_2$—COOH); 4.20-4.30 (multiplet, 5H, —$CH_2$—CH—$CH_2$—).
MS: M+1=951; M+23=974 (M+$Na^+$); M+39=990 (M+$K^+$).

Example 4e

Preparation of 1,2,3-tri-(tetradecylsulfonyl)acetylglycerol

This compound was obtained according to the procedure described hereinabove (example 4a) from tetradecylsulfonylacetic acid (example 1g) and glycerol.

Rf ($CH_2Cl_2$-Cyclohexane 7:3): 0.50.
IR: νCO ester 1741 $cm^{-1}$.
NMR ($^1H$, $CDCl_3$): 0.84-0.92 (t, 9H, —$CH_3$, J=6.7 Hz); 1.22-1.38 (multiplet, 60H, —$CH_2$—); 1.39-1.48 (multiplet, 6H, —$CH_2$—$CH_2$—$CH_2$—$SO_2$—); 1.81-1.94 (multiplet, 6H, —$CH_2$—$CH_2$—$SO_2$—); 3.21-3.30 (t, 6H, —$CH_2$—$CH_2$—$SO_2$—$CH_2$—COOH, J=8 Hz); 3.95 (s, 6H, —$CH_2$—$SO_2$—$CH_2$—COOH); 4.23-4.33 (multiplet, 5H, —$CH_2$—CH—$CH_2$—).

Example 4f

Preparation of 1,2,3-tri-tetradecylselenoacetylglycerol

This compound was obtained according to the procedure described hereinabove (example 4a) from tetradecylselenoacetic acid (example 1d) and glycerol.

Rf ($CH_2Cl_2$-Cyclohexane 7:3): 0.74.
IR: νCO ester 1737 and 1721 $cm^{-1}$.
NMR ($^1H$, $CDCl_3$): 0.85-0.92 (t, 9H, —$CH_3$, J=6.2 Hz); 1.23-1.46 (multiplet, 66H, —$CH_2$—); 1.62-1.76 (multiplet, 6H, —$CH_2$—$CH_2$—$CH_2$—Se—); 2.72-2.79 (t, 6H, $CH_2$—$CH_2$—Se, J=7.4 Hz); 3.15 (s, 6H, Se—$CH_2$—COOH); 4.13-4.23 (multiplet, 5H, —$CH_2$—CH—$CH_2$—).

Example 4g

Preparation of 1,3-dipalmitoyl-2-tetradecylthioacetylglycerol 1,3-dipalmitoylglycerol (5.64 g, 9.9 mmol, 1 eq), tetradecylthioacetic acid (5.74 g, 19.8 mmol, 2 eq), dicyclohexyl carbodiimide (4.1 g, 19.8 mmol, 2 eq) and dimethylaminopyridine (2.42 g, 19.8 mmol, 2 eq) were dissolved in dichloromethane. The reaction mixture was stirred at room temperature for 3 days. The dicyclohexylurea formed was filtered and washed several times with dichloromethane. The filtrate was dried. The residual product was purified by silica gel chromatography (eluent:dichloromethane/cyclohexane 4:6) (yield: 80 %).

Rf ($CH_2Cl_2$-Cyclohexane 7:3): 0.32.
MP°: 60-62° C.
IR: νCO ester 1744 and 1730 $cm^{-1}$.
NMR ($^1H$, $CDCl_3$): 0.86-0.91 (t, 9H, —$CH_3$, J=6.6 Hz); 1.10-1.45 (multiplet, 70H, —$CH_2$—); 1.57-1.64 (multiplet, 6H, —$CH_2$—$CH_2$—$CH_2$—S— and OCO$CH_2$—$CH_2$); 2.30-2.35 (t, 4H, OCO$CH_2$—$CH_2$—, J=7.4 Hz); 2.60-2.66 (t, 2H, $CH_2$—$CH_2$—S—, J=7.4 Hz); 3.23 (s, 2H, S—$CH_2$—COOH); 4.14-4.21 (dd, 2H, —CHaHb—CH—CHaHb—, J=12 Hz and J=5.8 Hz); 4.30-4.36 (dd, 2H, —CHaHb—CH—CHaHb—, J=12 Hz and J=4 Hz); 5.26-5.33 (m, 1H, —CHaHb—CH—CHaHb—).

MS: M+23=861 (M+Na⁺); M+39=877 (M+K⁺); (M+H not detected).

Example 4h

Preparation of 1,3-dilinoleyl-2-tetradecylthioacetylglycerol

This compound was obtained according to the procedure described hereinabove (example 4g) from 1,3-dilinoleylglycerol (example 3b) and tetradecylthioacetic acid (example 1a). The product was obtained as a colorless, viscous oil (yield: 56%).

Rf (CH$_2$Cl$_2$-Cyclohexane 7:3): 0.32.

IR: νCO ester 1745 cm⁻¹.

NMR (¹H, CDCl$_3$): 0.82-0.93 (t, 9H, —CH$_3$, J=6.6 Hz); 1.15-1.45 (multiplet, 50H, —CH$_2$—); 1.52-1.70 (multiplet, 6H, —CH$_2$—CH$_2$—CH$_2$—S— and OCOCH$_2$—CH$_2$); 1.93-2.14 (multiplet, 8H, —CH$_2$—CH=CH—CH$_2$—); 2.28-2.37 (t, 4H, OCOCH$_2$—CH$_2$—, J=7.5 Hz); 2.59-2.67 (t, 2H, CH$_2$—CH$_2$—S—, J=7.4 Hz); 2.70-2.83 (t, 4H, —CH$_2$—CH=CH—CH$_2$—CH=CH—CH$_2$—); 3.22 (s, 2H, S—CH$_2$—COOH); 4.12-4.23 (dd, 2H, —CHaHb—CH—CHaHb—, J=12 Hz and J=6.2 Hz); 4.28-4.37 (dd, 2H, —CHaHb—CH—CHaHb—, J=12 Hz and J=4 Hz); 5.24-5.45 (m, 1H, —CHaHb—CH—CHaHb—).

MS: M+23=909 (M+Na⁺); M+39=925 (M+K⁺); (M+H not detected).

Example 4i

Preparation of 1,3-distearyl-2-tetradecylthioacetylglycerol

This compound was obtained according to the procedure described hereinabove (example 4g) from 1,3-distearylglycerol (compound 3c) and tetradecylthioacetic acid (compound 1a).

Yield: 41%.

Rf (CH$_2$Cl$_2$): 0.32.

IR: νCO ester 1744 and 1731 cm⁻¹.

NMR (¹H, CDCl$_3$): 0.86-0.91 (t, 9H, —CH$_3$, J=6.6 Hz); 1.10-1.45 (multiplet, 78H, —CH$_2$—); 1.57-1.64 (multiplet, 6H, —CH$_2$—CH$_2$—CH$_2$—S— and OCOCH$_2$—CH$_2$); 2.29-2.35 (t, 4H, OCOCH$_2$—CH$_2$—, J=7.4 Hz); 2.60-2.66 (t, 2H, CH$_2$—CH$_2$—S—, J=7.4 Hz); 3.23 (s, 2H, S—CH$_2$—COOH); 4.14-4.21 (dd, 2H, —CHaHb—CH—CHaHb—, J=12 Hz and J=5.8 Hz); 4.30-4.36 (dd, 2H, —CHaHb—CH—CHaHb—, J=12 Hz and J=4 Hz); 5.26-5.32 (m, 1H, —CHaHb—CH—CHaHb—)

Example 4i

Preparation of 1,3-oleyl-2-tetradecylthioacetylglycerol

This compound was obtained according to the procedure described hereinabove (example 4g) from 1,3-dioleylglycerol (compound 3d) and tetradecylthioacetic acid (compound 1a).

The product was obtained as a colorless, viscous oil (yield: 32%).

Rf (CH$_2$Cl$_2$-Cyclohexane 7:3): 0.50.

IR: νCO ester 1746 cm⁻¹.

NMR (¹H, CDCl$_3$): 0.89 (t, 9H, —CH$_3$, J=6.4 Hz); 1.31 (multiplet, 62H, —CH$_2$—); 1.60 (multiplet, 6H, —CH$_2$—CH$_2$—CH$_2$—S— and OCOCH$_2$—CH$_2$); 2.02 (multiplet, 8H, —CH$_2$—CH=CH—CH$_2$—); 2.33 (t, 4H, OCOCH$_2$—CH$_2$—, J=7.3 Hz); 2.63 (t, 2H, CH$_2$—CH$_2$—S—, J=7.7 Hz); 3.23 (s, 2H, S—CH$_2$—COOH); 4.18 (dd, 2H, —CHaHb—CH—CHaHb—, J=12.4 Hz and J=6.4 Hz); 4.33 (dd, 2H, —CHaHb—CH—CHaHb—, J=12.4 Hz and J=4.5 Hz); 5.33 (multiplet, 1H, —CHaHb—CH—CHaHb— and —CH$_2$—CH=CH—CH$_2$—).

MS: M+23=913 (M+Na⁺); M+39=929 (M+K⁺); (M+H not detected).

Example 4k

Preparation of 1,3-ditetradecanoyl-2-tetradecylthioacetylglycerol

This compound was obtained according to the procedure described hereinabove (example 4g) from 1,3-ditetradecanoylglycerol (compound 3e) and tetradecylthioacetic acid (compound 1a). (yield: 28%).

Rf (CH$_2$Cl$_2$-Cyclohexane 7:3): 0.30.

MP°: 60-62° C.

IR: νCO ester 1744 and 1730 cm⁻¹.

NMR (¹H, CDCl$_3$): 0.87 (t, 9H, —CH$_3$, J=7.2 Hz); 1.27 (multiplet, 62H, —CH$_2$—); 1.60 (multiplet, 6H, —CH$_2$—CH$_2$—CH$_2$—S— and OCOCH$_2$—CH$_2$); 2.33 (t, 4H, OCOCH$_2$—CH$_2$—, J=7.7 Hz); 2.63 (t, 2H, CH$_2$—CH$_2$—S—, J=7.2 Hz); 3.23 (s, 2H, S—CH$_2$—COOH); 4.18 (dd, 2H, —CHaHb—CH—CHaHb—, J=12 Hz and J=5.8 Hz); 4.33 (dd, 2H, —CHaHb—CH—CHaHb—, J=11.5 Hz and J=5.8 Hz); 5.30 (m, 1H, —CHaHb—CH—CHaHb—).

MS: M+23=805 (M+Na⁺); (M+H not detected).

Example 4i

Preparation of 1-palmitoyl-2,3-ditetradecylthioacetylglycerol

Glycerol 1-palmitate (4.804 g, 0.014 mol) was dissolved in dichloromethane (300 ml) and dicyclohexylcarbodiimide (7.498 g, 0.036 mol), dimethylaminopyridine (4.439 g, 0.036 mol) and tetradecylthioacetic acid (8.386 g, 0.029 mol) were then added. The reaction mixture was stirred at room temperature for 48 hours. The dicyclohexylurea precipitate was filtered and washed with dichloromethane. The filtrate was dried. The residue was purified by silica gel chromatography (eluent:dichloromethane-cyclohexane 4-6) to give the desired compound as a white powder (yield: 42%).

Rf (CH$_2$Cl$_2$-Cyclohexane 7-3): 0.31.

MP°: 57-59° C.

IR: νCO ester 1736 and 1722 cm⁻¹.

NMR (¹H, CDCl$_3$): 0.89 (t, 9H, —CH$_3$, J=6.6 Hz); 1.27 (multiplet, 68H, —CH$_2$—); 1.60 (multiplet, 6H, —CH$_2$—CH$_2$—CH$_2$—S— and OCOCH$_2$—CH$_2$); 2.33 (t, 2H, OCOCH$_2$—CH$_2$—, J=7 Hz); 2.63 (t, 4H, CH$_2$—CH$_2$—S—, J=8.9 Hz); 3.23 (s, 4H, S—CH$_2$—COOH); 4.23 (m, 2H, —CHaHb—CH—CHaHb—); 4.37 (m, 2H, —CHaHb—CH—CHaHb); 5.31 (m, 1H, —CHaHb—CH—CHaHb—).

MS: M+23=893 (M+Na⁺); M+39=909 (M+K⁺); (M+H not detected).

Example 4m

Preparation of 1-oleyl-3-palmitoyl-2-tetradecylthioacetylglycerol 3-oleyl-1-palmitoylglycerol (2 g, 0.003 mol) was dissolved in dichloromethane (150 ml) and dicyclohexylcarbodiimide (1.040 g, 0.005 mol), dimethylaminopyridine (0.616 g, 0.005 mol) and tetradecylthioacetic acid (1.455 g, 0.005 mol) were then added. The mixture was stirred at room temperature for 24 hours. The dicyclohexylurea precipitate was filtered, washed with dichloromethane and the filtrate was concentrated. The residue obtained was purified by silica gel chromatography (eluent:$CH_2Cl_2$-cyclohexane 4:6) to give the desired compound as an oil (yield: 49%).

Rf ($CH_2Cl_2$-Cyclohexane 7:3): 0.45.
MP°<4° C.
IR: νCO ester 1742 $cm^{-1}$.
NMR ($^1H$, $CDCl_3$): 0.89 (t, 9H, —$CH_3$, J=6.5 Hz); 1.26 (multiplet, 66H, —$CH_2$—); 1.60 (multiplet, 6H, —$CH_2$—$CH_2$—$CH_2$—S— and $OCOCH_2$—$CH_2$); 2.03 (multiplet, 4H, —$CH_2$—CH=CH—$CH_2$—); 2.33 (t, 4H, $OCOCH_2$—$CH_2$—, J=7.4 Hz); 2.63 (t, 2H, $CH_2$—$CH_2$—S—, J=7.4 Hz); 3.23 (s, 2H, S—$CH_2$—COOH); 4.18 (dd, 2H, —CHaHb—CH—CHaHb—, J=12.2 Hz and J=6.1 Hz); 4.33 (dd, 2H, —CHaHb—CH—CHaHb—, J=12.2 Hz and J=4.4 Hz); 5.32 (multiplet, 3H, —CHaHb—CH—CHaHb— and —$CH_2$—CH=CH—$CH_2$—).
MS: M+23=887 ($M+Na^+$); M+39=903 ($M+K^+$); (M+H not detected).

Example 4n

Preparation of 1,3-dipalmitoyl-2-docosylthioacetylglycerol

This compound was obtained according to the procedure described hereinabove (example 4g) from 1,3-dipalmitoylglycerol (example 3a) and docosylthioacetic acid (example 1i).

Yield: 77%.
Rf ($CH_2Cl_2$-Cyclohexane 7:3): 0.32.
IR: νCO ester 1745 and 1730 $cm^{-1}$.
NMR ($^1H$, $CDCl_3$): 0.86-0.91 (t, 9H, —$CH_3$, J=6.6 Hz); 1.10-1.45 (multiplet, 86H, —$CH_2$—); 1.57-1.64 (multiplet, 6H, —$CH_2$—$CH_2$—$CH_2$—S— and $OCOCH_2$—$CH_2$); 2.29-2.34 (t, 4H, $OCOCH_2$—$CH_2$—, J=7.5 Hz); 2.60-2.66 (t, 2H, $CH_2$—$CH_2$—S—, J=7.4 Hz); 3.23 (s, 2H, S—$CH_2$—COOH); 4.13-4.22 (dd, 2H, —CHaHb—CH—CHaHb—, J=12 Hz and J=5.8 Hz); 4.30-4.36 (dd, 2H, —CHaHb—CH—CHaHb—, J=12 Hz and J=4 Hz); 5.27-5.34 (m, 1H, —CHaHb—CH—CHaHb—).

Example 5

Preparation of 2-aminoglycerol Derivatives

Example 5a

Preparation of 2-tetradecylthioacetamidopropane-1,3-diol

Tetradecylthioacetic acid (2.878 g, 0.010 mol) and 2-amino-1,3-propanediol (1 g, 0.011 mol) were placed in a flask and heated at 190° C. for 1 hour. After cooling to room temperature, the medium was taken up in chloroform and washed with water. The organic phase was dried on $MgSO_4$, filtered then evaporated to form a solid ochre residue. This residue was stirred in diethyl ether for 12 hours. The product was isolated by filtration in the form of a white powder (yield: 6%).

Rf ($CH_2Cl_2$-methanol 9:1): 0.60.
MP°: 95-97° C.
IR: νCO amide 1640 $cm^{-1}$.
NMR ($^1H$, $CDCl_3$): 0.84-0.93 (t, 3H, —$CH_3$, J=6.4 Hz); 1.21-1.45 (multiplet, 22H, —$CH_2$—); 1.54-1.72 (m, 2H, —$CH_2$—$CH_2$—$CH_2$—S—); 2.52-2.59 (t, 2H, $CH_2$—$CH_2$—S—, J=7.1 Hz); 2.63 (sl, 2H, OH); 3.27 (s, 2H, S—$CH_2$—COOH); 3.77-3.96 (multiplet, 4H, —$CH_2$—CH—$CH_2$—); 3.97-4.04 (m, 1H, —$CH_2$—CH—$CH_2$—); 7.55 (d, 1—CONH—, J=6.7 Hz).
MS: M+1=362; M+23=384 ($M+Na^+$); M+39=400 ($M+K^+$).

Example 5b

Preparation of 2-tetradecylthioacetamido-1,3-ditetradecylthioacetyloxypropane 2-tetradecylthioacetamidopropan-1,3-diol (1 g, 2.77 mmol) (example 5a) was dissolved in dichloromethane (180 ml), then dicyclohexycarbodiimide (1.427 g, 6.91 mmol), dimethylaminopyridine (0.845 g, 6.91 mmol) and tetradecylthioacetic acid (1.995 g, 6.91 mmol) (example 1a) were added in that order. The reaction mixture was stirred at room temperature for 48 hours. The dicyclohexylurea precipitate was filtered and washed with dichloromethane and the filtrate was concentrated. The residue obtained was purified by silica gel chromatography (eluent:dichloromethane-cyclohexane 7:3). The desired compound was obtained as a white powder (yield: 66%).

Rf ($CH_2Cl_2$ 10): 0.18.
MP°: 82-84° C.
IR: νCO ester 1715 and 1730 $cm^{-1}$; νCO amide 1648 $cm^{-1}$.
NMR ($^1H$, $CDCl_3$): 0.84-0.95 (t, 3H, —$CH_3$, J=6.6 Hz); 1.221-1.45 (multiplet, 66H, —$CH_2$—); 1.54-1.69 (multiplet, 6H, —$CH_2$—$CH_2$—$CH_2$—S—); 2.48-2.55 (t, 2H, $CH_2$—$CH_2$—S—$CH_2$—CONH—, J=7.5 Hz); 2.59-2.70 (t, 4H, $CH_2$—$CH_2$—S—$CH_2$—COO—, J=7.2 Hz); 3.24 (s, 6H, S—$CH_2$—CO—); 4.18-4.35 (multiplet, 4H, —$CH_2$—CH—$CH_2$—); 4.47-4.60 (m, 1H, —$CH_2$—CH—$CH_2$—); 7.23 (d, 1H, —CONH—, J=8.5 Hz).
MS: M+23=924 ($M+Na^+$); (M+1 not detected).

Example 6

Method of Solubilization of Triacylglycerols According to the Invention

The inventive compounds described in examples 2 to 5 may be solubilized as described for example 4a.

Such solubilization is useful for conducting in vitro experiments.

An emulsion comprising the compound of example 4a and phosphatidylcholine (PC) was prepared as described by Spooner et al. (Spooner et al., JBC, 1988, 263: 1444-1453). Compound 4a was mixed with PC in a 4:1 (m/m) ratio in chloroform, the mixture was dried under nitrogen, then vacuum evaporated overnight; the resulting powder was taken up in 0.16 M KCl containing 0.01 M EDTA and the lipid particles were dispersed by ultrasound for 30 minutes at 37° C. The liposomes so formed were then separated by ultracentrifugation (XL 80 ultracentrifuge, Beckman Coulter, Villepinte, France) at 25,000 rpm for 45 minutes to recover liposomes having a size greater than 100 nm and close to that of chylomicrons. Liposomes composed only of PC were prepared concurrently to use as negative control.

The concentration of compound 4a in the liposomes was estimated by using the enzyme colorimetric triglyceride assay kit. The assay was carried out against a standard curve, prepared with the lipid calibrator CFAS, Ref. 759350 (Boehringer Mannheim GmbH, Germany). The standard curve covered concentrations ranging from 16 to 500 µg/ml. 100 µl of each sample dilution or calibration standard were deposited per well on a titration plate (96 wells). 200 µl of triglyceride reagents, ref. 701912 (Boehringer Mannheim GmbH, Germany) were then added to each well, and the entire plate was incubated at 37° C. for 30 minutes. Optical densities (OD) were read on a spectrophotometer at 492 nm. Triglyceride concentrations in each sample were calculated from the standard curve plotted as a linear function $y=ax+b$, where y represents OD and x represents triglyceride concentrations.

Liposomes of compound 4a, prepared in this manner, can be used for in vitro experiments.

Example 7

Evaluation of PPAR Activation In Vitro

The inventive compounds tested are the compounds whose preparation is described in examples 2 to 5 hereinabove.

Nuclear receptors of the PPAR subfamily, which are activated by two major drug classes—fibrates and glitazones, widely used in the clinic for the treatment of dyslipidemiae and diabetes—play an important role in lipid and glucose homeostasis. In particular, the PPARα receptor modulates, among other things, the expression of genes encoding the apolipoproteins involved in lipid transport and the expression of the genes ACO on the one hand, and CPT-I and CPT-II on the other hand, respectively involved in peroxisomal and mitochondrial β-oxidation. The following examples demonstrate that the inventive compounds activate PPARα and PPARγ in vitro.

Activation of the PPARs was evaluated in vitro in primary rat hepatocyte cultures by measuring the expression of PPAR target genes and by measuring the transcriptional activity of a chimera composed of the DNA binding domain of the yeast Gal4 transcription factor and the ligand binding domain of the different PPARs. These latter results were then confirmed in cell lines by the protocols described hereinbelow.

1) Primary Hepatocyte Cultures
   a. Culture Protocol

Rat hepatocytes were isolated from male OFA Wistar rats (Charles River, L'Arbresle, France) weighing between 175 and 225 g by perfusion of the liver with a mixture of collagenase and thermolysin (Blendzyme 3, Roche, Basel, Switzerland). The livers of rats under pentobarbital anesthesia were perfused through the portal vein, first with 100 ml of perfusion buffer (Liver perfusion medium, Gibco, Paisley, UK) and then with 200 ml of the following digestion medium: HBSS depleted of $CaCl_2$ and $MgSO_4$ (Sigma, St. Louis, Mo., USA) supplemented with 10 mM Hepes, pH 7.6, 4 mM $CaCl_2$ and 7 mg of Blendzyme 3 according to a modification of the previously described protocol (Raspé et al., J. Lipid Res. 40, 2099-2110, 1999). When cell viability as measured by the trypan blue test (Sigma, St Louis, Mo., USA) exceeded 80%, hepatocytes were spread in 24-well culture dishes at a rate of $7.5 \times 10^4$ cells/cm$^2$ for transfection experiments or in 6-well culture dishes at $10^5$ cells/cm$^2$ for quantification of messenger RNA. Cells were seeded and incubated for 4 hours in Williams E culture medium supplemented with 100 U/ml penicillin (Gibco, Paisley, UK), 2 mM L-glutamine (Gibco, Paisley, UK), 2% (VN) UltroSER SF (Biosepra, Cergy St-Christophe, France), 0.2% (mN) bovine serum albumin (Sigma, St Louis, Mo., USA), 1 µM dexamethasone (Sigma, St Louis, Mo., USA) and 100 nM T3 (Sigma, St Louis, Mo., USA). The experiment was then continued in the same culture medium depleted of Ultroser. The test compounds were added at the indicated concentration directly to the culture medium.

b. Transfection Protocol

Rat hepatocytes isolated and cultured as described hereinabove were transfected overnight in culture medium depleted of Ultroser with the reporter plasmid pG5TkpGL3 (10 ng/well), the pGal4-φ, pGal4-mPPARα, pGal4-hPPARα, pGal4-hPPARγ, pGal4-hPPARδ expression vectors (10 ng/well) and the transfection efficiency control vector pRL-Null (1 ng/well) (Promega, Madison, Wis., USA) by means of lipofectin (Gibco, Paisley, UK) or Effecten (Qiagen, Courtaboeuf, France) according to the supplier's protocol. After transfection, cells were treated and incubated for 36 hours as previously described (Raspé et al., J. Lipid Res. 40, 2099-2110, 1999). At the end of the experiments, cells were lysed and luciferase activity was assayed with the Dual-Luciferase™ Reporter Assay System (Promega, Madison, Wis., USA) according to the supplier's instructions as previously described (Raspé et al., J. Lipid Res. 40, 2099-2110, 1999). The protein concentration in the cell extracts was then determined with the Bio-Rad Protein Assay kit (Bio-Rad, Munich, Germany) according to the supplier's instructions.

c. Description of Plasmids

Plasmids pG5TkpGL3, pGal4-hPPARα, pGal4-hPPARγ and pGal4-φ have been described previously (Raspé et al., J. Lipid Res. 40, 2099-2110, 1999). The pGal4-mPPARα and pGal4-hPPARδ constructs were obtained by cloning PCR-amplified DNA fragments corresponding to the DEF domains of the mouse PPARα and human PPARδ nuclear receptors into the pGal4-φ vector.

d. Messenger RNA Quantification

Messenger RNA was extracted from the primary rat hepatocytes with Tri-Reagent (Sigma, St Louis, Mo., USA) according to the supplier's instructions, assayed by spectrophotometry and quantified by semi-quantitative or quantitative RT-PCR using the Light Cycler Fast Start DNA Master Sybr Green I kit (Hoffman-La Roche, Basel, Switzerland) on a Light Cycler System (Hoffman-La Roche, Basel, Switzerland). Primer pairs specific for the ACO and Apo AII genes, PPARα targets, were used as probes. Primer pairs specific for the 36B4, β-actin and GAPDH genes were used as control probes (see table I hereinbelow).

TABLE I

| Name | Sequence | Semi quantitative PCR | | Quantitative PCR | | Gene |
|---|---|---|---|---|---|---|
| | | Tm | No. cycle | Tm | No. cycle | |
| ApoAI_r_1_s 741 | GCCTGAATCTCCTGGACAACTG | 58° C. | 25 | 58° C. | 18 to 20 | Apo AI |
| ApoAI_r_1_as 742 | ATGCCTTTGCATCTCCTTCG | | | | | |
| ApoB_r_1_s 743 | ATACAGCCTGAGTGAGCCTCTTCAG | 55° C. | 30 | X | X | Apo B |
| ApoB_r_1_as 744 | CCAGGGAGTTGGAGACCGTG | | | | | |
| GAPDH_h_1_s 390 | GACATCAAGAAGGTGGTGAA | 55° C. | 25 | 55° C. | 20 (variable) | GAPDH |
| GAPDH_h_1_as 389 | CCACATACCAGGAAATGAGC | | | | | |
| beta-actin_h_1_s 189 | TTCAACTCCATCATGAAGTGTGAC | 55° C. | 25 | 55° C. | variable | β actin |
| beta-actin_h_1_as 188 | TCGTCATACTCCTTGCTTGCTGATCC | | | | | |
| CPT1_r_1_s 517 | GCTGGCTTATCGTGGTGGTG | 60° C. | 25 | 60° C. | 20 to 25 | CPT-I |
| CPT1_r_1_as 516 | GACCTGAGAGGACCTTGACC | | | | | |
| 36B4_h_1_s 177 | CATGCTCAACATCTCCCCCTTCTCC | X | X | 55° C. | 23 | 36B4 |
| 36B4_h_1_as 178 | GGGAAGGTGTAATCCGTCTCCACAG | | | | | |
| ACOX1_r_1_as 457 | CGCATCCATTTCTCCTGCTG | 60° C. | 25 | 60° C. | 18 to 24 | ACO |
| ACOX1_r_1_s 458 | TTCTGTCGCCACCTCCTCTG | | | | | |
| ApoCIII_r_1_s 797 | ATGCAGCCCCGAATGCTCCTCATCGTGG | 55° C. | 30 | 55° C. | 28 to 30 | Apo CIII |
| ApoCIII_r_1_as 798 | TCACGGCTCAAGAGTTGGTGTTAC | | | | | |
| CPT2_r_1_s 725 | CAGAAGCCTCTCTTGGATGACAG | 55° C. | 25 | X | X | CPT-II |
| CPT2_r_1_as 726 | TTGGTTGCCCTGGTAAGCTG | | | | | |

TABLE I-continued

| Name | Sequence | Semi quantitative PCR Tm | Semi quantitative PCR No. cycle | Quantitative PCR Tm | Quantitative PCR No. cycle | Gene |
|---|---|---|---|---|---|---|
| ABCA1_h_2_s | CTGAGGTTGCTGCTG TGGAAG | 65° C. | 21 | X | X | ABCA1 |
| ABCA1_h_2_as | CATCTGAGAACAGGC GAGCC | | | | | |

2) Cell Lines a. Culture Protocols

HepG2 and RK13 cells were from ECACC (Porton Down, UK) and were grown in DMEM medium supplemented with 10% (V/V) fetal calf serum, 100 U/ml penicillin (Gibco, Paisley, UK) and 2 mM L-glutamine (Gibco, Paisley, UK). The culture medium was replaced every two days. Cells were kept at 37° C. in a humidified 5% $CO_2$/95% air atmosphere.

b. Transfection

HepG2 and RK13 cells seeded in 24-well culture dishes at a rate of $10^5$ cells/well for HepG2 cells and $5 \times 10^4$ cells/well for RK13 cells were transfected for 2 hours with the reporter plasmid pG5TkpGL3 (10 ng/well), the expression vectors pGal4-φ, pGal4-mPPARα, pGal4-hPPARα, pGal4-hPPARγ, pGal4-hPPARδ (10 ng/well) and the transfection efficiency control vector pRL-null (Promega Madison, Wis., USA) (20 ng/well) according to the protocol previously described (Raspé et al., J. Lipid Res. 40, 2099-2110, 1999) and incubated for 36 hours with the test compounds. At the end of the experiment, cells were lysed (Gibco, Paisley, UK) and luciferase activity was assayed with the Dual-Luciferase™ Reporter Assay System (Promega, Madison, Wis., USA) according to the supplier's instructions as previously described (Raspé et al., J. Lipid Res. 40, 2099-2110, 1999). Protein concentrations in the cell extracts were then determined with the Bio-Rad Protein Assay kit (Bio-Rad, Munich, Germany) according to the supplier's instructions.

The results are presented in FIG. 11. They show that the test compounds induce a very strong activation of the PPARα nuclear receptor.

Example 8

Evaluation of the Effects on Lipid Metabolism In Vivo

The inventive compounds tested are the compounds whose preparation is described in examples 2 to 5 hereinabove.

Fibrates, widely used in human medicine for the treatment of dyslipidemiae involved the development of atherosclerosis, one of the leading causes of morbidity and mortality in industrialized countries, are potent activators of the PPARα nuclear receptor. The latter regulates the expression of genes involved in the transport (apolipoproteins such as Apo AI, ApoAII and ApoC-III, membrane transporters such as FAT) or catabolism of lipids (ACO, CPT-I or CPT-II). Treatment of rodents with PPARα activators therefore leads to a decrease in plasma cholesterol and triglyceride levels.

The following protocols were designed to demonstrate a decrease in circulating triglyceride and cholesterol levels, and also highlight the interest of the inventive compounds for preventing and/or treating cardiovascular diseases.

1) Treatment of Animals

Sprague-Dawley or Wistar rats weighing 200 to 230 g (Charles River, L'Arbresle, France) were housed in a 12-hour light/dark cycle at a constant temperature of 20±3° C. After a 1-week acclimatization period, rats were weighed and distributed into groups of 8 animals selected such that the distribution of plasma cholesterol and triglyceride levels was uniform. The test compounds were suspended in carboxymethylcellulose and administered by gastric lavage at the indicated doses, once a day for 15 days. Animals had access to food and water ad libitum. At the end of the experiments, animals were weighed and sacrificed under anesthesia after a 5-hour fast. Blood was collected on EDTA. Plasma was isolated by centrifugation at 3000 rpm for 20 minutes. Liver samples were removed and stored frozen in liquid nitrogen until further analysis.

2) Determination of Serum Lipids and Apolipoproteins

Lipid concentrations in plasma (total cholesterol and free cholesterol, triglycerides and phospholipids) were determined by a colorimetric assay (Bio-Mérieux, Marcy l'Etoile, France) according to the supplier's instructions. Plasma concentrations of apolipoproteins AII, AI and CIII were determined as previously described (Raspé et al., J. Lipid Res. 40, 2099-2110, 1999, Asset G et al., Lipids, 34, 39-44, 1999).

To separate the lipoproteins according to size, 300 µl of plasma were loaded on a Sepharose 6HR 10/30 column (Pharmacia, Uppsala, Sweden) and eluted at a constant flow rate (0.2 ml/minute) in PBS (pH 7.2). Optical density of the eluent was recorded at 280 nm. 0.3 ml fractions were collected. Lipid concentrations in the different fractions were determined by a colorimetric assay (Bio-Mérieux, Marcy l'Etoile, France) according to the supplier's instructions. The results are presented in FIGS. 2, 3, 4, 9A and 9B.

3) RNA Analysis

Total RNA was isolated from the liver fragments by extraction with a mixture of guanidine thiocyanate/phenol acid/chloroform as previously described (Raspé et al., J. Lipid Res. 40, 2099-2110, 1999). Messenger RNA was quantified by semi-quantitative or quantitative RT-PCR with the Light Cycler Fast Start DNA Master Sybr Green I kit (Hoffman-La Roche, Basel, Switzerland) on a Light Cycler System (Hoffman-La Roche, Basel, Switzerland). Primer pairs specific for the ACO, Apo CIII, Apo AI, CPT-I and CPT-II genes were used as probes. Primer pairs specific for the 36B4, β-actin and GAPDH genes were used as control probes (see table I).

The results are shown in FIGS. 5 and 9C.

Example 9

Evaluation of the Antioxidant Properties of the Inventive Compounds

The inventive compounds tested are the compounds whose preparation is described in examples 2 to 5 hereinabove.

Oxidation of LDL lies at the basis of the inflammatory process which leads to atherosclerosis and cardiovascular diseases. Compounds which delay or inhibit such oxidation therefore have beneficial protective effects.

1. Protection against LDL oxidation induced by copper or azobis(2-amidinopropane)dihydrochloride (AAPH):

Oxidation of LDL is an important modification which plays a major role in the onset and development of atherosclerosis (Jurgens, Hoff et al. 1987). The following protocol allows demonstration of the antioxidant properties of compounds. Unless otherwise indicated, all reagents were from Sigma (St Quentin, France).

LDL were prepared as described in Lebeau et al. (Lebeau, Furman et al. 2000).

The solutions of the test compounds were prepared so that the final concentration ranged from 1 to 100 µM with a total ethanol concentration of 1% (v/v).

Before oxidation, EDTA was removed from the LDL preparation by dialysis against PBS. The oxidation reaction was then carried out at 30° C. by adding 20 µl of a 16.6 µM $CuSO_4$ solution or a 2 mM MPH solution to 160 µl of LDL (125 µg protein/ml) and 20 µl of a test compound solution. The formation of dienes, the species to be followed, was measured by the optical density at 234 nm in the samples treated with the compounds but with or without copper (or MPH). Optical density at 234 nm was measured every 10 minutes for 8 hours on a thermostated spectrophotometer (Kontron Uvikon 930). The analyses were carried out in triplicate. The activity of the compounds was expressed as the percentage shift in the lag phase (latency time before the onset of oxidation) compared to that of the control. A compound was considered to have 100% antioxidant activity when it doubled the lag phase latency of the control sample. The applicants demonstrate that the inventive compounds, described in examples 2 to 5, delay LDL oxidation (induced by copper), indicating that said compounds possess intrinsic antioxidant activity.

2. Evaluation of the protection conferred by the inventive compounds against lipid peroxidation:

LDL oxidation was measured by the TBARS method.

According to the same principle as that described hereinabove, LDL were oxidized in the presence of $CuSO_4$ and lipid peroxidation was evaluated as follows:

TBARS were measured by a spectrophotometric method, lipid hydroperoxidation was measured by using lipid peroxide-dependent oxidation of iodide to iodine. The results are expressed as nmol of malondialdehyde (MDA) or as nmol hydroperoxide/mg protein.

The results obtained hereinabove by measuring the inhibition of conjugated diene formation, were confirmed by the experiments measuring LDL lipid peroxidation. The inventive compounds also afforded efficient protection of LDL against lipid peroxidation induced by copper (an oxidizing agent).

Example 9 demonstrates that the inventive compounds inhibit oxidative modification of LDL.

Example 10

Evaluation of Effects on the Expression of Enzymes Involved in Mitochondrial and Peroxisomal β-oxidation The inventive compounds tested are those whose preparation is described in examples 2 to 5 hereinabove.

Fatty acids are an essential reservoir of energy. Mitochondrial and peroxisomal β-oxidation of fatty acids are the main catabolic pathways whereby this energy is mobilized. These two processes therefore play a key role in controlling serum levels of free fatty acids and in regulating triglyceride synthesis. The rate-limiting enzyme for peroxisomal β-oxidation is ACO. Mitochondrial β-oxidation is limited by the transport of fatty acids into the mitochondria, which depends on the activity of the enzymes CPT-I and CPT-II. Regulation of the expression of enzymes ACO, CPT-I and CPT-II is a crucial step in controlling peroxisomal and mitochondrial β-oxidation, respectively.

The inventive compounds induce the expression of ACO, CPT-I and CPT-II. Said activity was demonstrated in the following manner:

RNA isolated from primary rat hepatocytes described in example 7 or from liver fragments removed from rats treated with the test compounds as described in example 8 was quantified by semi-quantitative or quantitative RT-PCR as described in examples 7 and 8 using primer pairs specific for the ACO, CPT-I and CPT-II genes.

Example 11

Evaluation of Fatty Acid Oxidation Capacities

The inventive compounds tested are those whose preparation is described in examples 2 to 5 hereinabove.

The oxidation capacities of fatty acids determine serum levels of free fatty acids as well as the potential for triglyceride synthesis. Accumulation of free fatty acids in blood or of triglycerides outside of adipose tissue predisposes to insulin resistance. Furthermore, elevated plasma triglyceride levels are now thought to be a risk factor for cardiovascular diseases. An increase in the oxidation capacities of fatty acids is therefore of therapeutic interest.

The inventive compounds activate fatty acid oxidation by mitochondria and peroxisomes. Said ability was demonstrated as follows:

Mitochondrial CPT-I and CPT-II activity was tested according to the method described in Madsen et al., 1999, Biochem. Pharmacol. 57, 1011-1019.

ACO activity was measured as in Asiedu et al., 1995, Eur. J. Biochem, 227, 715-722.

Mitochondrial and peroxisomal β-oxidation of fatty acids was evaluated as described in Hovik et al., 1990, Biochem. J. 270, 167-173.

Example 12

Evaluation of the Effects on Reverse Cholesterol Transport

The inventive compounds tested are those whose preparation is described in examples 2 to 5 hereinabove.

The negative correlation between HDL-cholesterol levels and cardiovascular diseases is now well established. The ability of a compound to increase reverse cholesterol transport (RCT) is considered a mechanism whereby HDL protect against atherosclerosis.

RCT is a process which allows excess cholesterol present in extrahepatic tissues to be recovered and exported to the liver where it undergoes transformation to bile acids which are then excreted in the bile.

The presence of macrophage-derived foam cells characterizes the first steps in the formation of atherosclerotic lesions.

Cholesterol outflow from macrophages is therefore a critical phase for preventing the formation of foam cells and, consequently, acts protectively against the development of atherosclerosis. The critical step of RCT is the transfer of excess cholesterol and cell membrane phospholipids to naiscent HDL. In this respect, the ABCA1 (ATP binding cassette A1) transporter plays a key role in this process and the expression thereof is correlated with a reduction in atherosclerotic plaque development through stimulation of cholesterol outflow from macrophages.

It was also recently shown that ABCA1 is a target gene of the LXRα nuclear receptor, itself a target gene of the PPARα and PPARγ receptors.

The inventive compounds induce the expression of LXRα and ABCA1 and stimulate cholesterol outflow in two in vitro models of primary and THP1 macrophages.

1/Measurement of ABCA1 and LXRα Expression:
a/Differentiation and Treatment of Primary and THP-1 Human Macrophages THP-1 monocytes (ATCC, Rockville, Md., USA) were placed in 6-well culture dishes in the presence of PMA (phorbol myristate acetate) and fetal calf serum and incubated at 37° C. for 48 hours to allow them to differentiate to macrophages.

To obtain primary macrophages, mononuclear cells were isolated from human blood as previously described (Chinetti et al. Nat. Medecine 7(1), 53-58, 2001), placed in 6-well culture dishes and grown for 10 days in the presence of human serum to enable adherence and differentiation of the primary monocytes to macrophages.

Treatment with the different compounds was carried out for 48 hours in medium without human or fetal calf serum but supplemented with 1% Nutridoma HU serum (Boehringer).

b/Messenger RNA Quantification

Total RNA was extracted from treated macrophages with the mini RNeasy kit (Qiagen, Hilden, Germany) according to the supplier's instructions, assayed by spectrometry and quantified by quantitative RT-PCR with the Light Cycler Fast DNA Master Green I kit (Hoffman-La Riche, Basel, Switzerland) on a Light Cycler System (Hoffman-La Riche, Basel, Switzerland). Primer pairs specific for the ABCA1 and LXRα genes were used as probes.

The results are shown in FIG. 12.

2/Measurement of Cholesterol Outflow:
a/Differentiation and Treatment of Primary and Human THP-1 Macrophages Macrophages were differentiated from THP-1 or primary monocytes as in the previous experiment (1—measurement of ABCA1 and LXRα expression).

b/Cholesterol Loading of Macrophages and Measurement of Outflow

Macrophages were pretreated for 24 hours with the compounds, but also every 24 hours throughout the duration of the experiment. Cholesterol loading was accomplished by incubation for 48 hours in the presence of acetylated LDL (50 μg/ml containing tritium-labelled cholesterol) in RPMI 1640 medium supplemented with 1% Nutridoma HU (Boehringer).

After this step, cells were washed twice with PBS and incubated for 24 hours in RPMI medium without Nutridoma, with or without apolipoprotein A-1. On completion of this step, the medium was recovered and intracellular lipids were extracted with a mixture of hexane/isopropanol, then dried under nitrogen. Outflow was quantified on a Tri-Carb® 2100 TR scintillation counter (Packard, Meriden, Conn., USA) by dividing the number of disintegrations counted in the medium by the total number of disintegrations counted in the medium and in the cells.

Example 13

Evaluation of the Effects on Metabolic Syndrome (Syndrome X) and Diabetes

The inventive compounds tested are those whose preparation is described in examples 2 to 5 hereinabove.

Insulin resistance is the underlying basis of metabolic syndrome, which is characterized by glucose intolerance, hyperinsulinemia, dyslipidemia and hypertension. The combination of several cardiovascular risk factors which leads to an increased risk of cardiovascular disease secondary to atherosclerosis is responsible for most of the morbidity and mortality associated with type 2 diabetes. Pharmacological treatments of metabolic syndrome are therefore targeted chiefly at insulin resistance.

The inventive compounds attenuate the manifestations of metabolic syndrome (syndrome X), such as elevation of free fatty acids, hyperinsulinemia, hyperglycemia and the insulinemic response to glucose (glucose tolerance test), and of diabetes in two animal models of insulin resistance linked to metabolic syndrome:C57BL/6 mice maintained on a high fat diet, and obese Zucker rats (fa/fa). These properties were demonstrated as follows:

1) Treatment of Animals

Male C57BL/6 mice (Charles River, L'Arbresle, France) aged 6 weeks at the start of the experiments were randomly divided into groups of 6 animals such that body weight distribution was uniform. Mice were given a low-fat diet (UAR AO4), a high-fat diet (29% (m/m) coconut oil) or the same enriched diet supplemented with the test compounds. Obese male Zucker rats (fa/fa) or non obese rats (fa/+) aged 5 or 21 weeks (Charles River, L'Arbresle, France) were divided into groups of 8 animals selected such that the distribution of plasma cholesterol and triglyceride levels was uniform, and maintained on a standard diet. Animals were housed in a 12 hour light/dark cycle at a constant temperature of 20° C.±3° C. Animals had access to food and water ad libitum. Food intake and weight increase were recorded. The test compounds were suspended in carboxymethylcellulose and administered by gastric lavage at the indicated doses, once a day for 15 days. At the end of treatment, some animals underwent a glucose tolerance test as described hereinbelow. At the end of the experiment the other animals were weighed and sacrificed under anesthesia after a 5 hour fast. Blood was collected on EDTA. Plasma was prepared by centrifugation at 3000 rpm for 20 minutes. Liver samples were removed and stored frozen in liquid nitrogen for subsequent analysis.

2) Assay of Free Fatty Acids and Lipids

Free fatty acid levels vary in diabetic rats. Free fatty acid concentrations in serum or plasma were determined by a colorimetric enzymatic reaction "NEFA/FFA" WAKO (Labo Immuno Systems, Neuss, Germany) on serum or plasma.

Plasma lipid concentrations (total cholesterol and triglycerides) were determined by a colorimetric assay (Bio-Mérieux, Marcy l'Etoile, France) according to the supplier's instructions.

The results are presented in FIGS. 6 and 10.

3) Glycemia Assay

Blood glucose was determined by a colorimetric enzymatic assay (Sigma Aldrich, St Louis, Mo., USA).

The results are given in FIG. 7.

4) Insulin Assay

To demonstrate hyperinsulinemia characteristic of metabolic diseases, insulin levels were assayed with a radioassay kit (Mercodia, Uppsala, Sweden). Insulinemia was assayed on serum or plasma collected on EDTA.

The results are given in FIG. 7.

5) Glucose Tolerance Test

Animals were anaesthetized after an 8 hour fast by intraperitoneal injection of pentobarbital sodium (50 mg/kg). To initiate the glucose tolerance test, glucose (1 g/kg) was injected into the peritoneal cavity before collecting blood samples from the caudal vein into heparinized tubes at 0, 15, 30, 45, and 60 minutes after the glucose load. Samples were stored on ice, the plasma was isolated and stored at −20° C. pending analysis.

The results are shown in FIG. 8.

Example 14

Evaluation of the Effects on Obesity

The inventive compounds tested are those whose preparation is described in examples 2 to 5 hereinabove.

Obesity is accompanied by an increase in insulin resistance, type 2 diabetes and an increased risk of cardiovascular disease and cancer. It therefore plays a central role in some of the pathologies prevalent in the industrialized world and, for this reason, poses a major pharmacological challenge.

The inventive compounds reduce weight gain in two animal models of obesity C57BL/6 mice fed a high-fat diet, and obese Zucker rats (fa/fa). These properties were demonstrated as follows:

1) Treatment of Animals

Male C57BL/6 mice (Charles River, L'Arbresle, France) aged 6 weeks at the start of the experiments were randomly divided into groups of 6 animals such that body weight distribution was uniform. Mice were given a low-fat diet (UAR AO4), a high-fat diet (29% (m/m) coconut oil) or the same enriched diet supplemented with the test compounds. Obese male Zucker rats (fa/fa) or non obese rats (fa/+) aged 5 weeks (Charles River, L'Arbresle, France) were divided into groups of 8 animals selected such that the distribution of plasma cholesterol and triglyceride levels was uniform, and maintained on a standard diet supplemented with the test compounds for 15 days. Animals were housed in a 12 hour light/dark cycle at a constant temperature of 20° C.±3° C. Animals had access to food and water ad libitum. Food intake and weight increase were recorded. At the end of the experiment the animals were weighed and sacrificed under anaesthesia. Plasma was prepared by centrifugation at 3000 rpm for 20 minutes. Liver and adipose tissue samples were removed, weighed and stored frozen in liquid nitrogen for subsequent analysis 2) Assay of Leptin Leptin, an obesity marker, was measured by the "Rat Leptin assay" kit from Linco Research (St Charles, Mich., USA).

Example 15

Evaluation of the Effects on Cell Growth

The inventive compounds tested are the compounds whose preparation is described in examples 2 to 5 hereinabove.

The inventive compounds decrease the growth of tumor cells.

This activity was observed by using the protocol described in Hvattum et al., Biochem. J. 294, 917-921,1993.

Example 16

Evaluation of the Effects of the Compounds on Restenosis

The inventive compounds tested are the compounds whose preparation is described in examples 2 to 5 hereinabove.

Proliferation of smooth muscle cell is one of the principal components of atherogenesis, restenosis and hypertension associated with cardiovascular disease. The identification of inhibitors of said proliferation is therefore a worthwhile challenge in pharmacology.

The inventive compounds decrease the growth of vascular smooth muscle cells in vitro and reduce restenosis in vivo in a rat balloon angioplasty model. These properties were demonstrated as follows:

1) Measurement of Smooth Muscle Cell Proliferation.

Smooth muscle cells from the coronary artery or aorta were from Promocell (Heidelberg, Germany) and were grown according to the supplier's instructions in a special smooth muscle cell culture medium supplemented with 10% fetal calf serum. Cells grown to 50% confluence were made quiescent by omitting the serum for 24 hours. Cells were then treated for 3 to 6 days in the presence of mitogens (10% serum, 20 ng/ml βPFGF or 2 U/ml α-thrombin) and the inventive compounds. At the end of the experiment, cells were trypsinized and counted on a hemocytometer.

2) Measurement of Restenosis in a Rat Balloon Coronary Angioplasty Model.

Adult Sprague-Dawley rats weighing 200 to 300 g (Iffa Credo, L'Arbresle, France) were housed in a 12 hour light/dark cycle at a constant temperature of 20° C.±3° C. After a 1-week acclimatization period, rats were weighed and divided into groups of 6 animals selected such that body weight distribution was uniform. The left internal coronary artery was damaged with a balloon as previously described (Ruef et al., Arterioscl., Thromb. and Vasc. Biol. 20,1745-1758, 2000). The inventive compounds were suspended in carboxymethylcellulose and administered by gastric lavage at different doses, once a day for 4, 10 and 21 days. Animals had access to food and water ad libitum. Animals were then sacrificed and the coronary arteries fixed and analyzed as previously described (Ruef et al., Arterioscl., Thromb. And Vasc. Biol. 20,1745-1758, 2000).

Example 17

Evaluation of the Effects of the Compounds on Hypertension

The inventive compounds tested are the compounds whose preparation is described in examples 2 to 5 hereinabove.

Hypertension is a major risk factor for cardiovascular disease and represents an important pharmacological challenge.

The inventive compounds lower blood pressure in vivo when administered to spontaneously hypertensive rats (SHR rats) in a model of hypertension. These properties were demonstrated in the following manner:

1) Treatment of Animals

Adult SHR rats weighing 200 to 300 g (Harlan France, Gannat, France) were housed in a 12-hour light/dark cycle at a constant temperature of 20° C.±3° C. After a 1-week acclimatization period, rats were weighed and divided into groups of 6 animals selected such that body weight distribution was uniform. The inventive compounds were suspended in carboxymethylcellulose and administered by gastric lavage at different doses, once a day for 7 days. Animals had access to food and water ad libitum.

2) Blood Pressure Measurement

Blood pressure was measured according to the protocol described in Siragy and Carey (J. Clin. Invest., 100, 264-269, 1997).

Example 18

Evaluation of Antioxidant Properties on Cell Cultures

The inventive compounds tested are the compounds whose preparation is described in examples 2 to 5 hereinabove.

a) Procurement and Culture of Normal Human Keratinocytes

Normal human keratinocytes (NHK) were cultured from skin samples. The sample was first washed four times in PBS (Phosphate Buffered Saline—Invitrogen, France), then decontaminated by immersion for 30 seconds in two successive baths of 70% ethanol. Strips 3 mm wide were then cut, taking care to remove as much adipose tissue and dermis as possible. The strips were then incubated in a 0.25% trypsin solution (Invitrogen, France) at 37° C. for 4 hours. After separation of epidermis from dermis, the epidermal preparation was filtered and centrifuged at 1000 rpm for 5 minutes. The pellet was taken up in KHN-D medium (DMEM+10% fetal calf serum (FCS)+hydrocortisone 0.4 µg/ml+EGF 10 ng/ml+$10^{-9}$ M cholera toxin (Sigma, St Quentin, France)). Cells were counted, then seeded at $10 \times 10^6$ cells/75 cm$^2$.

After 24 hours of culture, the medium was changed, cells were washed in PBS and K-SFM culture growth medium (Invitrogen, France) was then subsequently used. Cells were seeded at the desired density. Cells were grown in a 5% $CO_2$ atmosphere at 37° C. and the culture medium was changed every 48 hours. Treatment with or without the inventive compounds took place before the cells reached confluence (70-80%), at which time the compounds were added directly to the culture medium at concentrations ranging from 1 to 100 µM.

b) Procurement and Culture of Human Fibroblasts

Normal human fibroblasts were cultured from skin samples. The samples were first washed 4 times in PBS (Phosphate Buffered Saline—Invitrogen, France), then decontaminated by immersion for 30 seconds in two successive baths of 70% ethanol. Pieces of dermis having an area of about 5 mm$^2$ were placed on the bottom of a Petri dish. Once the pieces adhered to the support (approximately 5 minutes), they were covered with 4 ml of DMEM medium supplemented with 20% FCS. The medium was replaced every two days. Cells migrated from the explant after one week and colonized the Petri dish. Once the cells had colonized the support, they were trypsinized, reseeded and cultured in DMEM+10% FCS (Invitrogen, France) at 37° C. in a 5% $CO_2$ atmosphere. Cells were treated when they reached confluence, the inventive compounds being added directly to the culture medium at concentrations ranging from 1 to 100 µM.

c) Messenger RNA Quantification mRNA was extracted from the normal human keratinocyte and fibroblast cultures treated or not with the inventive compounds. Extraction was carried out with the reagents in the Absolutely RNA RT-PCR miniprep kit (Stratagene, France) according to the supplier's instructions. mRNA was then assayed by spectrometry and quantified by quantitative RT-PCR using the Light Cycler Fast Start DNA Master Sybr Green I kit (Roche) on a Light Cycler System (Roche, France). Primer pairs specific for the genes encoding superoxide dismutase (SOD) and glutathione peroxidase (GPx), two antioxidant enzymes, were used as probes. Primer pairs specific for the 36B4, β-actin and GAPDH genes were used as controls (see Table I).

d) Determination of Glutathione Peroxidase (GPx) Activity

Glutathione peroxidase activity was measured on protein extracts of cells (keratinocytes, fibroblasts) treated or not with the inventive compounds at concentrations ranging from 1 to 100 µM. GPx activity was also determined under conditions of cellular stress (0.5 mM paraquat or 0.6 mM $H_2O_2$, which induce the formation of reactive oxygen species). Activity in the protein extracts was measured with the Glutathione Peroxidase Cellular Activity Assay Kit (Sigma) according to the supplier's instructions. Indirect determination is based on oxidation of glutathione to oxidized glutathione catalyzed by glutathione peroxidase. Reconversion to the non-oxidated form is catalyzed by glutathione reductase and NADPH (β-nicotinamide adenine dinucleotide phosphate). The decrease in NADPH absorbance is measured at 340 nm on a Shimazu 1501 spectrofluorimeter (Shimadzu Corporation, Kyoto, Japan) and reflects GPx activity, since GPx is the limiting factor in this reaction.

e) Determination of Lipid Peroxidation

Reagents were from Sigma (St Quentin, France) unless otherwise indicated. Lipid peroxidation was measured by assaying malondialdehyde (MDA) using thiobarbituric acid (TBA). After the treatments, the cellular supernatant was collected (900 µl) and 90 µl of butylated hydroxytoluene were added (Morliere P. et al. (1991), UVA-induced lipid peroxidation in cultured human fibroblasts. *Biochim Biophys Acta* 1084, 261-8). One milliliter of a 0.375% solution of TBA in 0.25 M HCl containing 15% trichloroacetic acid was also added to the supernatant. The mixture was heated at 80° C. for 15 minutes, cooled on ice and the organic phase was extracted with butanol. The organic phase was analyzed by spectrofluorimetry (λex=515 nm and λem=550 nm), on a Shimazu 1501 spectrofluorimeter (Shimadzu Corporation, Kyoto, Japan). TBARS were expressed as MDA equivalents using tetra-ethoxypropane as standard. The results were normalized against the protein content of the cells. Lipid peroxidation was induced by treating the wells with 0.5 mM paraquat (inducer of reactive oxygen species) or 0.6 mM hydrogen peroxide for 4 hours. The anti-radical protection provided by the inventive compounds at concentrations of 1 to 100 µM was evaluated by a 24-hour pretreatment, before induction of lipid peroxidation.

Example 19

Evaluation of Anti-inflammatory Properties on Reconstructed Epidermis

Reconstructed epidermis was supplied by SkinEthic (Nice, France). Epidermis was used at day 17 (0.63 cm$^2$) when the horny layer was present and the epithelial ultra-structure resembled that of human epidermis in vivo. Reconstructed epidermis was maintained in culture as instructed by the supplier. The reconstructed epidermis was treated with the inventive compounds at doses ranging from 2 to 10 mg/cm$^2$ for 24 and 72 hours.

The inventive compounds tested are the compounds whose preparation is described in examples 2 to 5 hereinabove.

a) Measurement of Anti-inflammatory Properties

The reconstructed epidermis was preincubated with the inventive compounds at concentrations ranging from 2 to 10 mg/cm$^2$ for 24 hours, then treated with 0.4%. SDS or 1 µg of TPA (12-O-tetradecanoylphbrbol-13-acetate) for 6 hours. The anti-inflammatory potential of the compounds was evaluated by an ELISA method. The culture media (below) of the control or treated epidermis were collected and frozen at −20° C. Interleukin 1-α (IL1-α) was quantified with the ELISA IL1-α Kit (R&D System, UK) according to the supplier's instructions.

b) Messenger RNA Quantification mRNA was extracted from the reconstructed epidermis treated or not with the inventive compounds as described hereinabove. Extraction was carried out with the reagents of the Absolutely RNA RT-PCR Miniprep Kit (Stratagene) according to the supplier's instructions and mRNA was then assayed by spectrometry and quantified by quantitative RT-PCR using the Light Cycler Fast Start DNA Master Sybr Green I kit (Roche) on a Light Cycler System (Roche). Primer pairs specific for the IL1 (interleukin 1) and IL6 genes were used as probes. Primer pairs specific for the 36B4, β-actin and GAPDH genes were used as control probes (see Table I).

Example 20

Evaluation of Antioxidant Properties on Reconstructed Epidermis

Reconstructed epidermis was supplied by SkinEthic (Nice, France). Epidermis was used at day 17 (0.63 cm$^2$) when the horny layer was present and the epithelial ultra-structure resembled that of human epidermis in vivo. Reconstructed epidermis was maintained in culture as instructed by the supplier. The reconstructed epidermis was treated with the inventive compounds at doses ranging from 2 to 10 mg/cm$^2$ for 24 and 72 hours.

The inventive compounds tested are the compounds whose preparation is described in examples 2 to 5 hereinabove.

a) Messenger RNA Quantification mRNA was extracted from keratinocytes (from the reconstructed epidermis treated or not with the inventive compounds). Extraction was carried out with the reagents of the Absolutely RNA RT-PCR Miniprep Kit (Stratagene) according to the supplier's instructions and mRNA was then assayed by spectrometry and quantified by quantitative RT-PCR using the Light Cycler Fast Start DNA Master Sybr Green I kit (Roche) on a Light Cycler System (Roche). Primer pairs specific for the genes encoding superoxide dismutase (SOD) and glutathione peroxidase (GPx), two antioxidant enzymes, were used as probes. Primer pairs specific for the 36B4, β-actin and GAPDH genes were used as controls (see Table I).

b) Determination of Glutathione Peroxidase (GPx) Activity

Glutathione peroxidase activity was measured on protein extracts of reconstructed epidermis treated or not with the inventive compounds (2 to 10 mg/cm$^2$). GPx activity was also determined under conditions of cellular stress (0.5 mM paraquat, an inducer of reactive oxygen species). Activity in the protein extracts was measured with the Glutathione Peroxidase Cellular Activity Assay Kit (Sigma) according to the supplier's instructions. Indirect determination is based on oxidation of glutathione to oxidized glutathione catalyzed by glutathione peroxidase. Reconversion to the non-oxidated form is catalyzed by glutathione reductase and NADPH (β-nicotinamide adenine dinucleotide phosphate). The decrease in NADPH absorbance is measured at 340 nm on a Shimazu 1501 spectrofluorimeter (Shimadzu Corporation, Kyoto, Japan) and reflects GPx activity, since GPx is the limiting factor in this reaction.

Example 21

Cosmetic Composition: Anti-aging Daytime Facial Cream

| | |
|---|---|
| Glyceryl stearate + PEG-100 stearate | 6.00% |
| Squalane | 3.00% |
| Hydrogenated polyisobutene | 3.00% |
| Glycerol tricaprylate/caprate | 3.00% |
| Glycerin | 2.00% |
| Octyl methoxycinnamate | 2.00% |
| Beeswax | 1.50% |
| Ketostearyl octanoate | 1.50% |
| Cetyl alcohol | 1.00% |
| Stearyl alcohol | 1.00% |
| Dimethicone | 1.00% |
| Xanthan gum | 0.20% |
| Carbomer | 0.15% |
| 1,2,3-tritetradecylthioacetylglycerol | 0.10% |
| Neutralizer | qs. |
| Preservatives | qs. |
| Fragrance, Coloring agents | qs. |
| Water | q.s. 100.00% |

Example 22

Cosmetic Composition: Anti-aging Facial Emulsion-gel

| | |
|---|---|
| Glycerin | 5.00% |
| Caprylic/capric/succinic triglycerides | 3.00% |
| Octyl methoxycinnamate | 1.00% |
| 1,3-dipalmitoyl-2-tetradecylthioacetylglycerol | 0.50% |

-continued

| | |
|---|---|
| Acrylates/C10-30 alkyl acrylate cross polymer | 0.50% |
| Wheat protein hydrolysate | 0.50% |
| Dimethicone copolyol | 0.50% |
| Neutralizer | q.s. |
| Preservatives | q.s. |
| Fragrance, coloring agents | q.s. |
| Water | q.s. 100.00% |

The invention claimed is:

1. A compound represented by general formula (I):

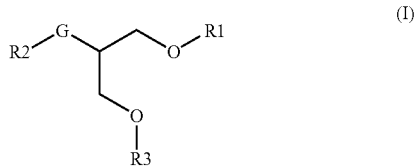

wherein

G represents an oxygen atom or a sulfur atom,

R1, R2 and R3, which are the same or different, represent (i) a hydrogen atom, (ii) a CO—R group in which R a linear or branched alkyl group, saturated or not, optionally substituted, the main chain of which contains from 1 to 25 carbon atoms, or (iii) a group having the formula CO—$(CH_2)_{2n+1}$—X—R' in which X is a sulfur atom, a selenium atom, an SO group or an $SO_2$ group, n is a whole number comprised between 0 and 11, and R' a linear or branched alkyl group, saturated or not, optionally substituted, the main chain of which contains from 13 to 23 carbon atoms and optionally one or more heterogroups selected in the group consisting of an oxygen atom, a sulfur atom, a selenium atom, an SO group and an $SO_2$ group, wherein at least one of the groups R1, R2 and R3 is a group having the formula CO—$(CH_2)_{2n+1}$—X—R' such as defined hereinabove.

2. A compound according to claim 1, wherein n is equal to 0.

3. The compound according to claim 1, wherein the R group or groups, which are the same or different, represent a linear or branched alkyl group, saturated or unsaturated, substituted or not, the main chain of which contains from 1 to 20 carbon atoms.

4. The compound according to claim 1, wherein the R' group or groups, which are the same or different, represent a linear or branched alkyl group, saturated or unsaturated, substituted or not, the main chain of which contains from 13 to 20 carbon atoms.

5. The compound according to claim 1, wherein the R group or groups, which are the same or different, are selected in the group consisting of $C_7H_{15}$, $C_{10}H_{21}$, $C_{11}H_{23}$, $C_{13}H_{27}$, $C_{14}H_{29}$, $C_{16}H_{33}$, $C_{17}H_{35}$, $C_{15}H_{31}$, $C_{20:5}$(5, 8, 11, 14, 17), $C_{22:6}$(4,7,10,13,16,19), $C_{14}H_{27}$, $C_{14}H_{25}$, $C_{15}H_{29}$, $C_{17}H_{29}$, $C_{17}H_{31}$, $C_{17}H_{33}$, $C_{19}H_{29}$, $C_{19}H_{31}$, $C_{21}H_{31}$, $C_{21}H_{35}$, $C_{21}H_{37}$, $C_{21}H_{39}$, $C_{23}H_{45}$, $(CH_2)_{n'}$—CH($CH_3$)$C_2H_5$, (CH=C($CH_3$)($CH_2$)$_2$)$_{n''}$—CH=C($CH_3$)$_2$ and $(CH_2)_{2x+1}$—C($CH_3$)$_2$—$(CH_2)_{n'''}$—$CH_3$, x being a whole number equal to or comprised between 1 and 11, n' being a whole number equal to or comprised between 1 and 22, n'' being a whole number equal to or comprised between 1 and 5, n''' being a whole number equal to or comprised between 0 and 22, and (2x+n''') being less than or equal to 22.

6. The compound according to claim 1, wherein the R' group or groups, which are the same or different, are selected in the group consisting of $C_{13}H_{27}$, $C_{14}H_{29}$, $C_{16}H_{33}$, $C_{17}H_{35}$, $C_{15}H_{31}$, $C_{20:5}$(5, 8, 11, 14, 17), $C_{22:6}$(4, 7, 10, 13, 16, 19), $C_{14}H_{27}$, $C_{14}H_{25}$, $C_{15}H_{29}$, $C_{17}H_{29}$, $C_{17}H_{31}$, $C_{17}H_{33}$, $C_{19}H_{29}$, $C_{19}H_{31}$, $C_{21}H_{31}$, $C_{21}H_{35}$, $C_{21}H_{37}$, $C_{21}H_{39}$, $C_{23}H_{45}$, $(CH_2)_{n'}$—CH($CH_3$)$C_2H_5$, (CH=C($CH_3$)($CH_2$)$_2$)$_{n''}$—CH=C($CH_3$)$_2$ and $(CH_2)_{2x+1}$—C($CH_3$)$_2$—$(CH_2)_{n'''}$—$CH_3$, x being a whole number equal to or comprised between 1 and 11, n' being a whole number equal to or comprised between 1 and 22, n'' being a whole number equal to or comprised between 1 and 5, n''' being a whole number equal to or comprised between 0 and 22, and (2x+n''') being less than or equal to 20.

7. The compound according to claim 1, wherein the R group or groups, which are the same or different, represent a lower alkyl group containing from 1 to 6 carbon atoms.

8. The compound according to claim 1, wherein the R' group or groups, which are the same or different, are saturated and linear alkyl groups containing from 13 to 17 carbon atoms.

9. The compound according to claim 1, wherein the alkyl groups are substituted by one or more substituents, which are the same or different, selected in the group consisting of a halogen atom (iodine, chlorine, fluorine, bromine) and a OH, =O, $NO_2$, $NH_2$, CN, $CH_2$—O, $CH_2OCH_3$, $CF_3$ and COOZ group in which Z is a hydrogen atom or an alkyl group containing from 1 to 6 carbon atoms.

10. The compound according to claim 1, wherein X is a sulfur or selenium atom.

11. The compound according to claim 1, wherein in the group CO—$(CH_2)_{2n+1}$—X—R', n is different from 1.

12. The compound represented by formula (I) according to claim 1, wherein at least one of the groups R1, R2 and R3 represents a CO—$(CH_2)_{2n+1}$—X—R' group in which X represents a selenium atom or a sulfur atom and/or R' is a saturated and linear alkyl group containing from 13 to 17 carbon atoms.

13. The compound according to claim 1, wherein R2 is a group corresponding to the formula CO—$(CH_2)_{2n+1}$—X—R' in which X represents a selenium atom or a sulfur atom and/or R' is a saturated and linear alkyl group containing from 13 to 17 carbon atoms.

14. The compound according to claim 1, wherein R2 is a group corresponding to the formula CO—$(CH_2)_{2n+1}$—X—R' in which X represents a selenium atom or a sulfur atom and/or R' is a saturated and linear alkyl group containing from 13 to 17 carbon atoms, and wherein R1 and R3, which are the same or different, represent a hydrogen atom.

15. The compound according to claim 1, wherein R2 is a group corresponding to the formula CO—$(CH_2)_{2n+1}$—X—R' in which X represents a selenium atom or a sulfur atom and/or R' is a saturated and linear alkyl group containing from 13 to 17 carbon atoms, and wherein R1 and R3, which are the same or different, represent a CO—R group.

16. The compound according to claim 1, wherein two of the groups R1, R2 and R3 are CO—$(CH_2)_{2n+1}$—X—R' groups, which are the same or different, in which X represents a selenium atom or a sulfur atom and/or R' is a saturated and linear alkyl group containing from 13 to 17 carbon atoms n is equal to 0.

17. The compound according to claim 1, wherein R1, R2 and R3, which are the same or different, are CO—$(CH_2)_{2n+1}$—X—R' groups, in which X represents a selenium atom or a sulfur atom and/or R' is a saturated and linear alkyl group containing from 13 to 17 carbon atoms.

18. The compound according to claim 1, wherein R1 is a group corresponding to the formula CO—(CH$_2$)$_{2n+1}$—X—R' in which X represents a selenium atom or a sulfur atom and/or R' is a saturated and linear alkyl group containing from 13 to 17 carbon atoms.

19. The compound according to claim 1, wherein R1 is a group corresponding to the formula CO—(CH$_2$)$_{2n+1}$—X—R', in which X represents a selenium atom or a sulfur atom and/or R' is a saturated and linear alkyl group containing from 13 to 17 carbon atoms, and wherein one and/or both groups R2 and R3 represent a hydrogen atom.

20. The compound according to claim 1, wherein R1 is a group corresponding to the formula CO—(CH$_2$)$_{2n+1}$—X—R', in which X represents a selenium atom or a sulfur atom and/or R' is a saturated and linear alkyl group containing from 13 to 17 carbon atoms, and wherein one and/or both groups R2 and R3 represent a CO—R group, which is the same or not.

21. The compound according to claim 1, wherein one of the groups R1, R2 or R3 is a COCH$_3$ group.

22. The compound according to claim 1, wherein the compound is selected from the group consisting of:

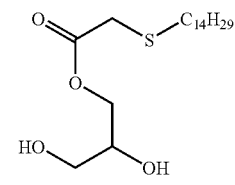
1A.2a

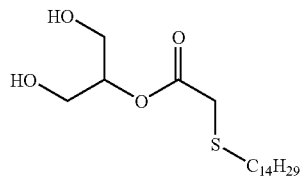
1A.2c

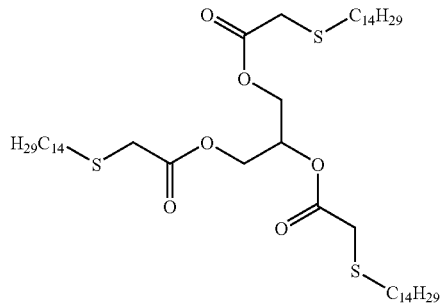
1A.4a

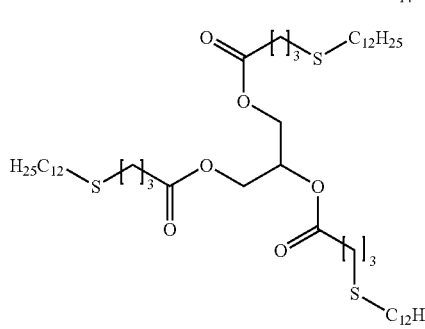
1A.4b

-continued

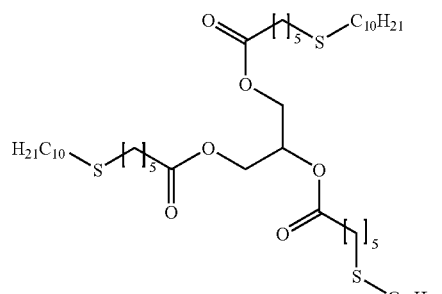
1A.4c

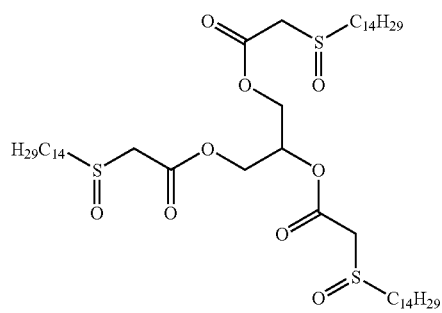
1A.4d

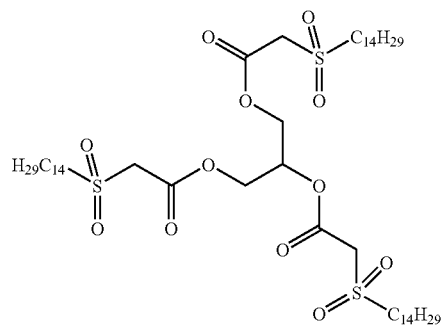
1A.4e

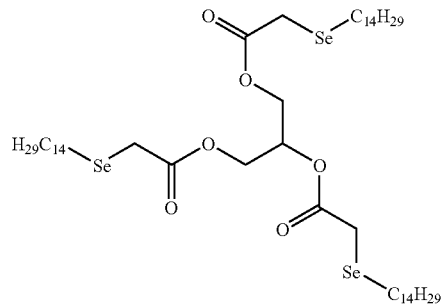
1A.4f

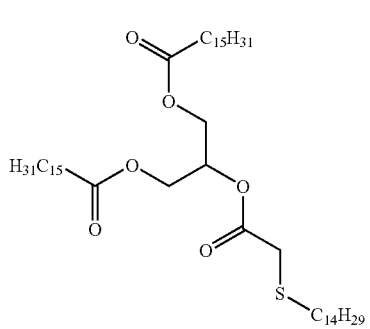
1A.4g

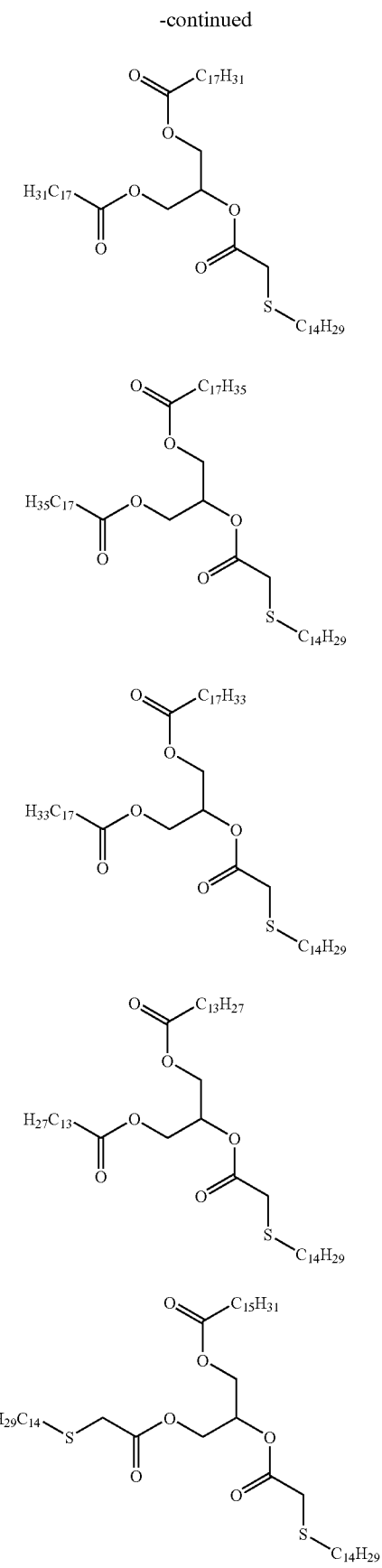
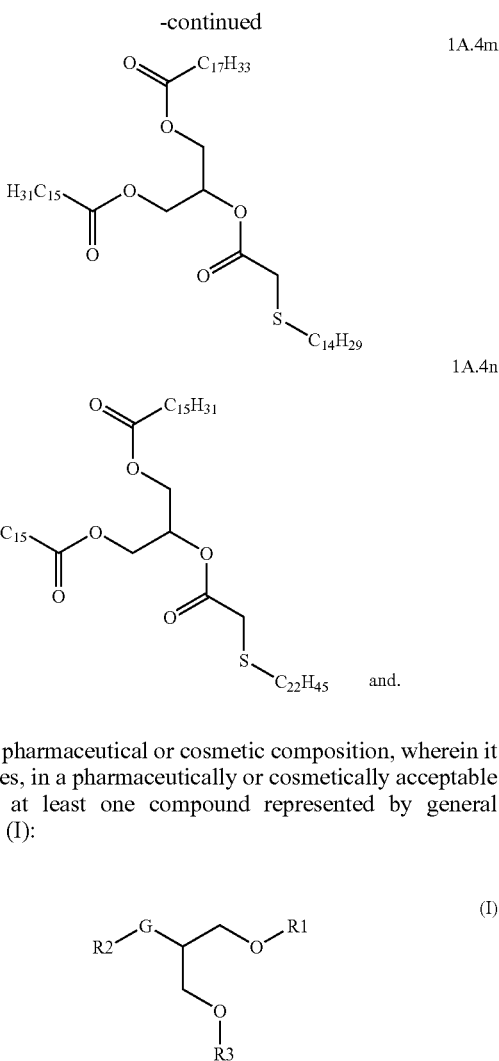

23. A pharmaceutical or cosmetic composition, wherein it comprises, in a pharmaceutically or cosmetically acceptable vehicle, at least one compound represented by general formula (I):

$$R2-G\underset{O-R3}{\overset{O-R1}{\diagup}} \quad (I)$$

wherein

G represents an oxygen atom or a sulfur atom,

R1, R2 and R3, which are the same or different, represent (i) a hydrogen atom, (ii) a CO—R group in which R is a linear or branched alkyl group, saturated or not, optionally substituted, the main chain of which contains from 1 to 25 carbon atoms, or (iii) a group corresponding to the formula CO—$(CH_2)_{2n+1}$—X—R' in which X is a sulfur atom, a selenium atom, an SO group or an $SO_2$ group, n is a whole number comprised between 0 and 11 and R' is a linear or branched alkyl group, saturated or not, optionally substituted, the main chain of which contains from 2 to 23 carbon atoms and optionally one or more heterogroups, selected in the group consisting of an oxygen atom, a sulfur atom, a selenium atom, an SO group or an $SO_2$ group, wherein at least one of the groups R1, R2 and R3 is a group corresponding to the formula CO—$(CH_2)_{2n+1}$—X—R' such as defined hereinabove.

24. The composition according to claim 23, wherein the compound is represented by formula (I) in which R' is a linear or branched alkyl group, saturated or not, optionally substituted, the main chain of which contains from 9 to 23 carbon atoms and optionally one or more heterogroups.

25. The composition according to claim 23, wherein the compound represented by formula (I) is defined in claim 1.

26. The compound according to claim 1, wherein n is equal to 1.

27. The composition according to claim 23, wherein n is equal to 0 or 1.

28. The compound according to claim 3, wherein said main chain contains from 7 to 17 carbon atoms.

29. The compound according to claim 8, wherein said saturated and linear alkyl groups contain from 14 to 16 carbon atoms.

30. The compound according to claim 8, wherein said saturated and linear alkyl groups contain 14 carbon atoms.

31. The compound according to claim 10, wherein X is a sulfur atom.

32. The compound according to claim 12, wherein said saturated and linear alkyl group contains from 14 to 16 carbon atoms.

33. The compound according to claim 12, wherein said saturated and linear alkyl group contains 14 carbon atoms.

34. The compound according to claim 13, wherein said $CO-(CH_2)_{2n+1}-X-R'$ is a group corresponding to the formula $CO-CH_2-S-C_{14}H_{29}$.

35. The compound according to claim 14, wherein said $CO-(CH_2)_{2n+1}-X-R'$ is a group corresponding to the formula $CO-CH_2-S-C_{14}H_{29}$.

36. The compound according to claim 15, wherein said $CO-(CH_2)_{2n+1}-X-R'$ is a group corresponding to the formula $CO-CH_2-S-C_{14}H_{29}$.

37. The compound according to claim 16, wherein said $CO-(CH_2)_{2n+1}-X-R'$ is a group corresponding to the formula $CO-CH_2-S-C_{14}H_{29}$.

38. The compound according to claim 17, wherein R1, R2 and R3 are the same and said $CO-(CH2)2n+1-X-R'$ is a group corresponding to the formula $CO-CH2-S-C14H29$.

39. The compound according to claim 18, wherein said $CO-(CH_2)_{2n+1}-X-R'$ is a group corresponding to the formula $CO-CH_2-S-C_{14}H_{29}$.

40. The compound according to claim 19, wherein said $CO-(CH_2)_{2n+1}-X-R'$ is a group corresponding to the formula $CO-CH_2-S-C_{14}H_{29}$.

41. The compound according to claim 20, wherein said $CO-(CH_2)_{2n+1}-X-R'$ is a group corresponding to the formula $CO-CH_2-S-C_{14}H_{29}$.

42. The compound according to claim 22, wherein the compound is:

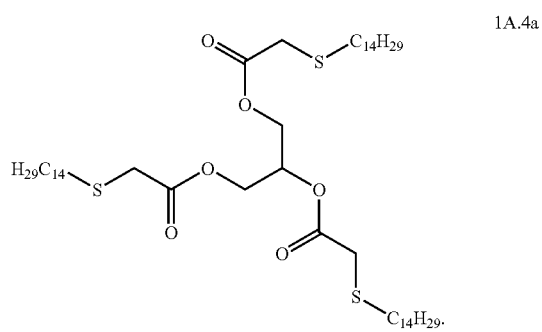

1A.4a

43. The composition according to claim 23, wherein it comprises at least the compound:

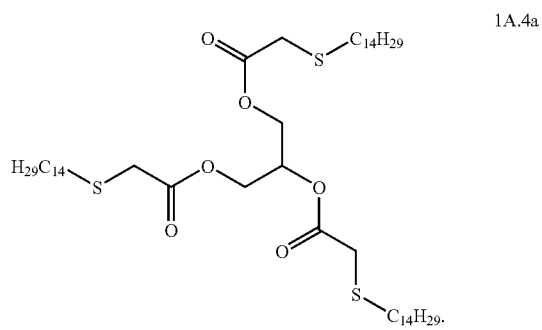

1A.4a

* * * * *